United States Patent
Zhou et al.

(10) Patent No.: US 10,474,646 B2
(45) Date of Patent: *Nov. 12, 2019

(54) SYSTEMS AND METHODS FOR CREATING A FORM FOR RECEIVING DATA RELATING TO A HEALTH CARE INCIDENT

(71) Applicant: RL SOLUTIONS, Toronto (CA)

(72) Inventors: Jian Zhou, North York (CA); Simon McKenna, Bellevue Heights (AU); Tom Belcher, Northgate (AU)

(73) Assignee: RLDATIX NORTH AMERICA INC., Toronto (CA)

( * ) Notice: Subject to any disclaimer, the term of this patent is extended or adjusted under 35 U.S.C. 154(b) by 237 days.

This patent is subject to a terminal disclaimer.

(21) Appl. No.: 15/705,923

(22) Filed: Sep. 15, 2017

(65) Prior Publication Data

US 2018/0018352 A1    Jan. 18, 2018

Related U.S. Application Data

(60) Continuation of application No. 14/295,637, filed on Jun. 4, 2014, now Pat. No. 9,798,747, which is a
(Continued)

(51) Int. Cl.
| | |
|---|---|
| *G06F 17/20* | (2006.01) |
| *G06F 16/21* | (2019.01) |
| *G16H 10/20* | (2018.01) |
| *G16H 15/00* | (2018.01) |
| *G06Q 50/22* | (2018.01) |

(52) U.S. Cl.
CPC .......... *G06F 16/211* (2019.01); *G06Q 50/22* (2013.01); *G16H 10/20* (2018.01); *G16H 15/00* (2018.01)

(58) Field of Classification Search
CPC ........ G06Q 50/22; G06Q 50/24; G06Q 40/08; G06F 16/211
See application file for complete search history.

(56) References Cited

U.S. PATENT DOCUMENTS

| | | |
|---|---|---|
| 5,583,758 A | 12/1996 | McIlroy et al. |
| 2006/0225032 A1 | 10/2006 | Klerk et al. |

(Continued)

FOREIGN PATENT DOCUMENTS

| | | |
|---|---|---|
| WO | 2008147616 A1 | 12/2008 |
| WO | WO-2008147616 A1 | 12/2008 |

OTHER PUBLICATIONS

Gall, W. et al., "A Clinical Form Designer", The 2001 International Conference on Mathematics and Engineering Techniques in Medicine and Biological Sciences, Jun. 25-28, 2001.
(Continued)

*Primary Examiner* — Mohammed H Zuberi
(74) *Attorney, Agent, or Firm* — Norton Rose Fulbright Canada LLP

(57) ABSTRACT

Embodiments of the invention relate to systems and methods for creating a form for receiving data relating to a health care incident. A dictionary of field objects is provided in a metabase, where a field object defines attributes, and an instance of a field object is a form field. A request to create a user-defined field object is received and it is determined that the user-defined field object is not in the dictionary of field objects in the metabase. The user-defined field object is generated by defining attributes for the user-defined field object, where at least one attribute is a presentation attribute for a form field within a form. The user-defined field object is added to the dictionary of field objects in the metabase and the user-defined field object is linked to a data location in a persistent store. The form is generated, where the form is an ordered collection of form fields, where at least one form field is an instance of the user-defined field object and is displayed according to the at least one presentation attribute.

21 Claims, 15 Drawing Sheets

Related U.S. Application Data division of application No. 13/070,754, filed on Mar. 24, 2011, now Pat. No. 8,781,852.

(60) Provisional application No. 61/317,504, filed on Mar. 25, 2010.

(56) References Cited

U.S. PATENT DOCUMENTS

| | | |
|---|---|---|
| 2006/0282291 A1 | 12/2006 | Runciman |
| 2007/0192678 A1 | 8/2007 | Tang et al. |
| 2007/0250783 A1 | 10/2007 | Wu et al. |
| 2012/0215560 A1 | 8/2012 | Ofek et al. |

OTHER PUBLICATIONS

Nadkarni, Prakash M. et al., "WebEAV: Automatic Metadata-Driven Generation of Web Interfaces to Entity-Attribute-Value Databases", Journal of the American Medical Informatics Association, vol. 7, No. 4, Jul.-Aug. 2000.

Extended European Search Report issued in EP Application No. 11159873.6 (dated Oct. 13, 2011).

Siika, An electronic medical record system for ambulatory care of HIV-infected patients in Kenya, International Journal of Medical Informatics, vol. 74, Issue 5, Jun. 2005, pp. 345-355.

USPTO, Office Action for U.S. Appl. No. 13/070,754 dated Aug. 15, 2013.

USPTO, Office Action for U.S. Appl. No. 14/295,637 dated Oct. 27, 2014.

USPTO, Office Action for U.S. Appl. No. 14/295,637 dated Mar. 27, 2015.

USPTO, Office Action for U.S. Appl. No. 14/295,637 dated Aug. 3, 2015.

USPTO, Office Action for U.S. Appl. No. 14/295,637 dated May 18, 2016.

USPTO, Office Action for U.S. Appl. No. 14/295,637 dated Oct. 6, 2016.

IP Australia, Office Action for AU Patent Application No. 2011201360 dated Nov. 12, 2015.

SYSTEMS AND METHODS FOR CREATING A FORM FOR RECEIVING DATA RELATING TO A HEALTH CARE INCIDENT

This application is a continuation of U.S. application Ser. No. 14/295,637, filed Jun. 4, 2014, which is a division of U.S. application Ser. No. 13/070,754, filed Mar. 24, 2011, which claims priority to U.S. Provisional Application No. 61/317,504, filed Mar. 25, 2010, the entire contents of which are hereby incorporated by reference.

FIELD

The described embodiments relate to systems and methods for creating a form, and in particular, relate to systems and methods for creating a form for receiving data relating to a health care incident.

BACKGROUND

Incidents commonly occur in health care facilities. For example, an incident may be a patient fall or a medication administration error. Incidents may relate to a wide range of activities that occur in health care facilities such as parking complaints, patient feedback, employee feedback, and the level of care provided at the health care facility.

An incident may involve a number of different people within the healthcare facility. For example, an incident may include doctors, nurses, patients, a patient's family members and administrators.

Typically, when an incident is recognized it is eventually reported to an administrator of the health care facility. The administrator may follow-up to inquire about the status of the incident, update any incident information and assign tasks to other workers in an attempt to resolve any outstanding issues related to the incident.

An administrator may use a health care incident management database to store data relating to incidents within a health care facility. Known health care incident management databases are based on a static set of data fields for storing data relating to the incident. This static set of data fields limits the number of data types available to the administrator. For example, the static set of fields may include only date of birth, name, weight, and height. An administrator may want to store a specific type of data in the health care incident management database that is not supported by the static set of data fields.

Administrators of such systems are left to re-task a data field in the static set of data fields. For example, if the administrator wanted to enter the date of the incident into the health care incident management database but only the data of birth was supported by the static set of data fields, then the administrator would re-task the date of birth data field to also store data values relating to the date of the incident. Re-tasking defined data fields may be problematic as the database would not distinguish between a data value that relates to the date of birth and a data value that relates to the date of the incident. This may lead to inefficiencies and errors in data storage, consolidation and comparison.

SUMMARY

In a first aspect, some embodiments of the invention provide a method for creating a form for receiving data relating to a health care incident, wherein the method is implemented on a processor and a memory storing instructions, the instructions being executable to configure the processor to perform operations comprising: providing a dictionary of field objects in a metabase, wherein a field object defines attributes, and wherein an instance of a field object is a form field; receiving a request to create a user-defined field object; determining that the user-defined field object is not in the dictionary of field objects in the metabase; generating the user-defined field object by defining attributes for the user-defined field object, wherein at least one attribute is a presentation attribute for a form field within a form; adding the user-defined field object to the dictionary of field objects in the metabase; linking the user-defined field object to a data location in a persistent store; and generating the form, wherein the form comprises an ordered collection of form fields, wherein at least one form field is configured to receive data relating to a health care incident, and wherein at least one form field is an instance of the user-defined field object and is displayed according to the at least one presentation attribute.

In some embodiments, the at least one form field that is the instance of the user-defined field object is configured to receive field value data, and the method further comprises: receiving field value data at the at least one form field that is the instance of the user-defined field object; determining the data location within the persistence store linked to the user-defined field object; and storing the received field value data as a field value at the data location linked to the user-defined field object.

In some embodiments, defining attributes corresponding to the user-defined field object comprises: providing a set of selectable attributes; receiving at least one selected attribute; and defining the at least one selected attribute as an attribute for the user-defined field object.

In some embodiments, the method includes: providing a set of selectable attribute values based on the selected attribute; receiving at least one selected attribute value; and linking the at least one selected attribute value to the selected attribute linked to the user-defined field object.

In some embodiments, the attributes are selected from the group consisting of: primary key identifier; version; last user to modify; time of last modification; table identifier; field name; field caption; field description; kind; database field name; field type; sequence; transient; allow null; unique; boolean default value; datetime default value; datetime mode; decimal default value; decimal is money; decimal precision; decimal scale; expression; kind of expression; identity auto increment; identity auto increment seed; identity auto increment step; identity default value; integer default value; number default value; text default value; maximum length of text; timespan default value; terminology provider; terminology namespace; terminology concept; mandatory; read-only; visible; extra parameters; list name; cachable; default value; security token; availability; field caption; control type; private; user created; identity use; inter default value and verification mask.

In some embodiments, the method includes generating a report using the field value corresponding to the user-defined field object.

In some embodiments, the method includes receiving a request to generate a report, where in the request comprises a user identifier and at least one search term; determining that the request comprising the at least one search term is a permitted search request using the user identifier; identifying a plurality of field objects for generating the report; determining that one or more of the plurality of field objects is forbidden to the user identifier; and generating the report using the plurality of field objects and excluding data corresponding to the one or more field objects forbidden to the user identifier.

In some embodiments, generating the form comprises: providing an initial set of selectable field objects; providing a search interface component configured to receive input data associated with a field object in the set of selectable field objects; receiving input data at the search interface component; determining an updated set of selectable field objects using the received input data; providing the updated set of selectable field objects, wherein the updated set of selectable field objects is a subset of the initial set of selectable field objects; receiving a selected field object from the updated set; and generating the form using the form field that is an instance of the selected field object.

In some embodiments, generating a form further comprises: receiving a request to generate the form, wherein the request comprises a user identifier; associating the user identifier with a user role, wherein the user role defines a data scope, wherein the data scope defines a set of permitted form fields; determining that the request to generate the form is a permitted search request according to the data scope associated with the user identifier; and limiting the collection of form fields in the form according to the data scope associated with the user identifier.

In some embodiments, the method includes: arranging the dictionary of field objects in the metabase as a tree of nodes, wherein each node corresponds to a field object; adding the user-defined field object to the dictionary of field objects as a parent node in the tree, wherein the parent node is associated with one or more child nodes; associating the user-defined field object with one or more forms; determining that the generated form comprises a form field that is an instance of the user-defined field object corresponding to the at least one parent node; and adding one or more additional form fields to the form, wherein the one or more additional form fields correspond to the one or more child nodes of the parent node corresponding to the user-defined field object.

In some embodiments, the form comprises a plurality of form fields configured to receive field value data, and wherein the method further comprises: providing a set of selectable field values for each of the plurality of form fields configured to receive field value data in the form, wherein each selectable field value corresponds to a potential field value associated with the corresponding field object; defining a matrix data structure for linking a field value for a first form field to a constrained set of selectable field values for each of the other form fields in the set of form fields, wherein the constrained set of selectable field values for each of the other form fields is a subset of the set of selectable field values for each of the other form fields, and wherein each of the constrained sets of selectable field values are related to the field value for the first form field; receiving a selected field value from the set of selectable field values for the first field object; and providing the constrained sets of selectable field values for each of the other form fields.

In another aspect, some embodiments provide a method for creating a form for receiving data relating to a health care incident: providing a dictionary of field objects in a metabase, wherein a field object defines attributes, wherein an instance of a field object is a form field, and wherein a form field is configured to receive a field value; generating a form, wherein the form comprises an ordered collection of form fields; providing a set of selectable field values for each form field in the form, wherein each selectable field value corresponds to a potential field value associated with the corresponding field object; defining a matrix data structure for linking a field value for a first form field to a constrained set of selectable field values for each of the other form fields in the form, wherein the constrained set of selectable field values for each of the other form fields is a subset of the set of selectable field values for each of the other form fields, and wherein each of the constrained sets of selectable field values are related to the field value for the first form field; receiving a selected field value from the set of selectable field values for the first field object; and providing the constrained sets of selectable field values for each of the other form fields.

In some embodiments, the method includes: defining the matrix data structure for linking a field value for a second form field to a constrained set of selectable field values for each of the other form fields in the form, wherein the constrained set of selectable field values for each of the other form fields is a subset of the set of selectable field values for each of the other form fields, and wherein each of the constrained sets of selectable field values are related to the field value for the second form field.

In some embodiments, the method includes: defining the matrix data structure for linking a field value for a second form field to a constrained set of selectable field values for each of the other form fields in the form, wherein the constrained set of selectable field values for each of the other form fields is a subset of the set of selectable field values for each of the other form fields, and wherein each of the constrained sets of selectable field values are related to the field value for the second form field.

In some embodiments, the method includes defining the matrix data structure for linking a field value for a third form field to a constrained set of selectable field values for each of the other form fields in the form, wherein the constrained set of selectable field values for each of the other form fields is a subset of the set of selectable field values for each of the other form fields, and wherein each of the constrained sets of selectable field values are related to the field value for the third form field.

In another aspect, some embodiments provide non-transitory computer-readable media upon which a plurality of instructions are stored, the instructions for performing the steps of the methods as described in relation to the various aspects and embodiments described above and below.

In another aspect, some embodiments provide a computer system for health care incident tracking comprising: an administrator application configured to execute instructions to provide: a user interface component configured to receive a request to create a form and to receive a request to create a user-defined field object; a persistent store configured to store health care incident data; at least one processor configured to execute instructions to provide: an interface module configured to receive a request to create a user-defined field object; and a metabase coupled to the persistent store, wherein the metabase is configured to: provide a dictionary of field objects in the persistent store, wherein an instance of a field object is a form field, wherein a field object defines attributes, and wherein at least one attribute is a presentation attribute for a form field within a form; determine that the user-defined field object is not in the dictionary of field objects; generate the user-defined field object by defining attributes for the user-defined field object, wherein at least one attribute is a display attribute for a form field within a form; add the user-defined field object to the dictionary of field objects; and link the user-defined field object to a data location in the persistent store; and a form engine configured to generate the form, wherein the form comprises an ordered collection of form fields, wherein at least one form field is configured to receive data relating to a health care incident, and wherein at least one form field is an instance of the user-defined field object and is displayed according to the at least one presentation attribute.

In some embodiments, the interface module is further configured to receive field value data at the at least one form field that is the instance of the user-defined field object; and wherein the metabase is further configured to store the received field value data as a field value at the data location linked to the user-defined field object.

In some embodiments, the interface module is further configured to provide a set of selectable attributes and receive at least one selected attribute; and wherein the metabase is further configured to define the at least one selected attribute as an attribute for the user-defined field object.

In some embodiments, the interface module is further configured to provide a set of selectable attribute values based on the selected attribute; receive at least one selected attribute value; and wherein the metabase is further configured to link the at least one selected attribute value to the selected attribute linked to the user-defined field object.

In some embodiments, the system includes a report engine configured to generate a report using the field value corresponding to the user-defined field object.

In some embodiments, the interface module is further configured to receive a request to generate a report, where in the request comprises a user identifier and at least one search term; and wherein the report engine is further configured to: determine that the request comprising the at least one search term is a permitted search request using the user identifier; identify a plurality of field objects for generating the report; determine that one or more of the plurality of field objects is forbidden to the user identifier; and generate the report using the plurality of field objects and excluding data corresponding to the one or more field objects forbidden to the user identifier.

In some embodiments, the interface module is further configured to: provide an initial set of selectable field objects; provide a search interface component configured to receive input data associated with a field object in the set of selectable field objects; receive input data at the search interface component; determine an updated set of selectable field objects using the received input data; provide the updated set of selectable field objects, wherein the updated set of selectable field objects is a subset of the initial set of selectable field objects; and receive a selected field object from the updated set; and wherein the form engine is further configured to generate the form using the form field that is an instance of the selected field object.

In some embodiments, the interface module is further configured to receive a request to generate the form, wherein the request comprises a user identifier; and wherein the form engine is further configured to: associate the user identifier with a user role, wherein the user role defines a data scope, wherein the data scope defines a set of permitted form fields; determine that the request to generate the form is a permitted search request according to the data scope associated with the user identifier; and limit the collection of form fields in the form according to the data scope associated with the user identifier.

In some embodiments, the form engine module is further configured to: provide a set of selectable field values for each of the plurality of form fields configured to receive field value data in the form, wherein each selectable field value corresponds to a potential field value associated with the corresponding field object; define a matrix data structure for linking a field value for a first form field to a constrained set of selectable field values for each of the other form fields in the set of form fields, wherein the constrained set of selectable field values for each of the other form fields is a subset of the set of selectable field values for each of the other form fields, and wherein each of the constrained sets of selectable field values are related to the field value for the first form field; receive a selected field value from the set of selectable field values for the first field object; and provide the constrained sets of selectable field values for each of the other form fields.

In some embodiments, the form engine is further configured to: define the matrix data structure for linking a field value for a second form field to a constrained set of selectable field values for each of the other form fields in the form, wherein the constrained set of selectable field values for each of the other form fields is a subset of the set of selectable field values for each of the other form fields, and wherein each of the constrained sets of selectable field values are related to the field value for the second form field.

In some embodiments, the form engine is further configured to: define the matrix data structure for linking a field value for a third form field to a constrained set of selectable field values for each of the other form fields in the form, wherein the constrained set of selectable field values for each of the other form fields is a subset of the set of selectable field values for each of the other form fields, and wherein each of the constrained sets of selectable field values are related to the field value for the third form field

BRIEF DESCRIPTION OF THE DRAWINGS

For a better understanding of the various embodiments described herein, and to show more clearly how they may be carried into effect, reference will now be made, by way of example only, to the accompanying drawings which show at least one exemplary embodiment, and in which:

FIG. 7 is a screen shot diagram of a form in accordance with an example embodiment;

FIG. 11 is a screen shot diagram of a user interface component for defining the matrix data structure in accordance with an example embodiment;

FIG. 12 is a screen shot diagram of a report in accordance with an example embodiment;

FIG. 13 is a screen shot diagram of a report with a forbidden field withheld from the report in accordance with an example embodiment.

Figure 1:
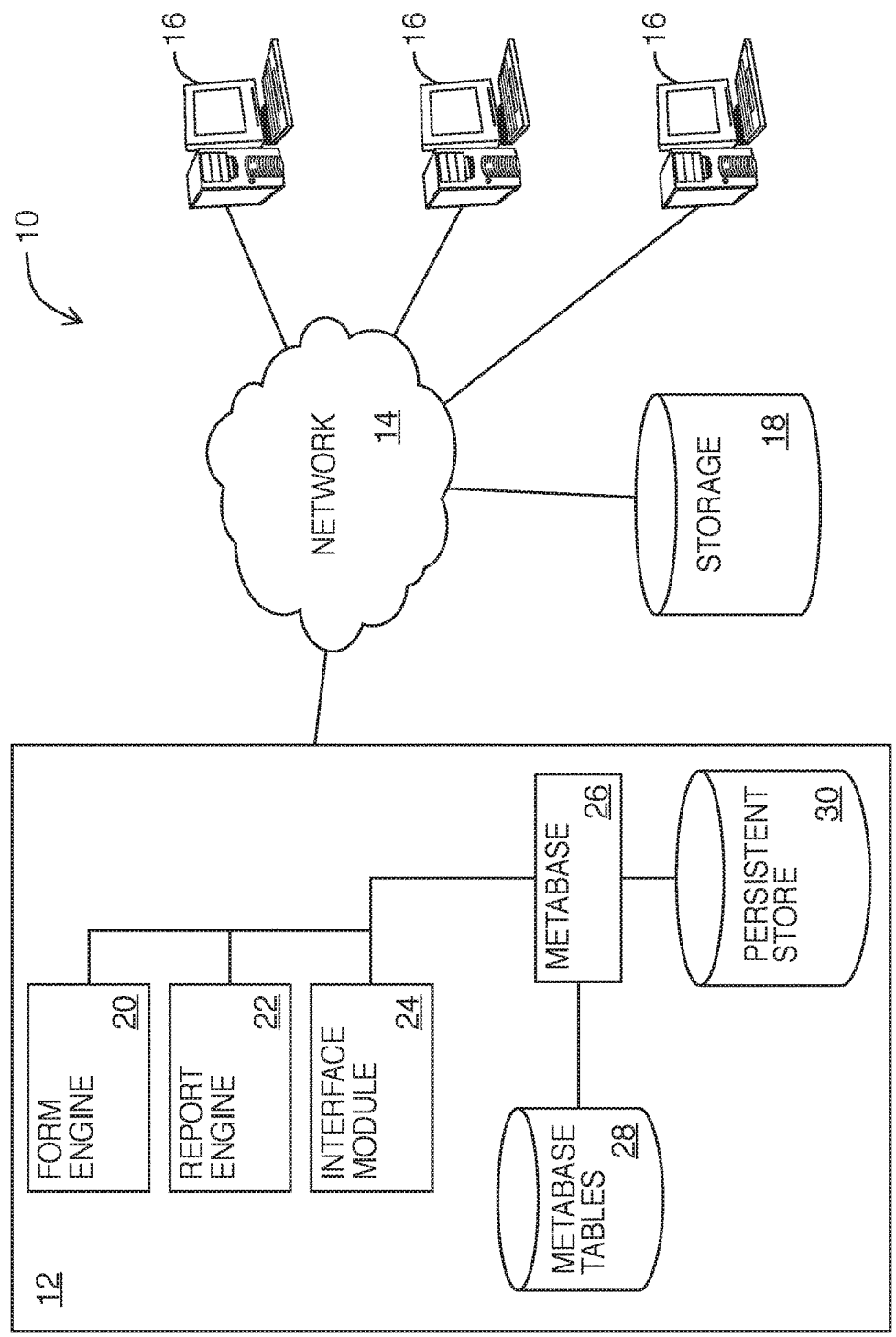
FIG. 1 a block diagram of a system for creating a form for receiving data in accordance with an example embodiment.

The skilled person in the art will understand that the drawings, described below, are for illustration purposes only. The drawings are not intended to limit the scope of the applicants' teachings in anyway. Also, it will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF EXEMPLARY EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The embodiments of the systems and methods described herein may be implemented in hardware or software, or a combination of both. However, preferably, these embodiments are implemented in computer programs executing on programmable computers each comprising at least one processor, a data storage system (including volatile and non-volatile memory and/or storage elements), and at least one communication interface. For example and without limitation, the programmable computers may be a server, network appliance, set-top box, embedded device, computer expansion module, personal computer, laptop, personal data assistant, or mobile device. Program code is applied to input data to perform the functions described herein and generate output information. The output information is applied to one or more output devices, in known fashion. In some embodiments, the communication interface may be a network communication interface. In embodiments where elements of the invention are combined, the communication interface may be a software communication interface, such as those for inter-process communication (IPC). In still other embodiments, there may be a combination of communication interfaces.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a physical computer readable medium that bears computer usable instructions for one or more processors. The medium may be provided in various forms, including one or more diskettes, compact disks, tapes, chips, magnetic and electronic storage media, and the like. The computer useable instructions may also be in various forms, including compiled and non-compiled code.

FIG. 1 is a block diagram of a system 10 for creating a form for receiving data relating to a health care incident in accordance with an example embodiment. System 10 includes a data system 12, workstations 16, and storage 18, connected via network 14.

Network 14 may be any network capable of carrying data, including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WMAX), SS7 signaling network, fixed line, local area network, wide area network, and others, including any combination of these, capable of interfacing with, and enabling communication between, data system 12, workstations 16, and storage 18.

Data system 12, workstations 16, and storage 18 may be connected to network 14 through a firewall (not shown), which is a device, set of devices or software that inspects network traffic passing through it, and denies or permits passage based on a set of rules and other criteria. Firewall may be adapted to permit, deny, encrypt, decrypt, or proxy all computer traffic between a communication network and an event system based upon a set of rules and other criteria. For example, firewall may be a network layer firewall, an application layer firewall, a proxy server, or a firewall with network address translation functionality.

Data system 12 has a processor and a memory storing instructions, the instructions being executable to configure the processor to provide a number of functional elements including: a form engine 20, a report engine 22, an interface module 24, a metabase 26, metabase tables 28 and a persistent store 30.

Storage 18 is a hardware and software storage system, which may include volatile and non-volatile memory and/or storage elements. Although shown connected to data system 12 and workstation 16 via network, storage 18 may be internal to workstation 16 and/or data system 12.

As an illustrative example, data system 12 will be described herein as a health care incident management system. However, data system 12 may be implemented in a wide variety of systems that collect, manage and report on incidents, risks and other applications requiring form and report generation.

At a high level, health care incident management system 12 is operable to receive data relating to health care incidents via forms displayed on workstations 16, for example, and store the received data in a metabase 26. Metabase 26 is operable to store a dictionary of field objects that are used to create forms. Metabase 26 is operable to store the field values received from completed forms in persistent store 30. Metabase tables 28 are used by metabase 26 to store attributes relating to the field objects. Each of the field objects extends the attributes of the corresponding physical object (i.e., received data), adding structure, meaning, and information that does not exist in its own right in the physical schema. Attributes may include how the field object may be represented within a form and the relationship between field objects and other field objects, users (represented by a user identifier), forms, and reports. Health care incident management system 12 is further operable to generate reports using the stored data for users, such as incident file summaries and patient records.

In an example embodiment, health care incident management system 12 has a processor and a memory storing instructions, the instructions being executable to configure the processor to provide a number of functional elements including: a form engine 20, a report engine 22, an interface module 24, and a metabase 26.

Form engine 20 is operable to generate a form, which is a collection of form fields operable to receive field values. For example, the form may relate to a health care incident involving a patient and the form fields are operable to receive field values pertaining to the health care incident. Health care incident management system 12 is operable to store received field values in a persistent store 30 (or storage 18) at a location linked to a corresponding field object. Form fields are instances of these field objects, as will be explained herein.

Report engine 22 is operable to generate reports using data stored in persistent store 30 and metabase 26, including the stored field values. A report may include text, tables, figures, pictures, attachments, abstracts, summaries, appendices, footnotes, hyperlinks, charts, graphs and the like. For example, the report may be a medical incident report outlining all health care incidents involving a specific patient. As another example, a report may provide a summary of field value data received in relation to a specific health care incident.

Interface Module 24 is operable to provide a user interface for creating user-defined field objects, creating forms, and generating reports by a user. In some embodiments, the user may communicate with interface module 24 via workstation 16.

Metabase 26 is operable to manage the structure and underlying knowledge of information in health care incident management system 12. Metabase 26 abstracts the persistence of data in the persistence store 30 so that the data is not tied to a single source or schema. The structure of the health care incident data is stored in metabase tables 28. For example, metabase 26 may indicate to health care incident management system 12 that a field object, such as a "Person" has a "Name" and a "Date of Birth". Metabase 26 may also indicate to health care incident management system 12 that a person's surname may be captioned as "Surname", "Last Name" or "Family Name" without making any changes to the underlying field value (e.g. the patient's actual surname) in the persistent store 30. Instead, this caption data associated with the underlying field values may be stored in metabase tables 28 and linked to the field values.

In some embodiments, metabase 26 is operable to maintain a logical relationship with the field values stored in persistent store 30. Meta-tables 110 may correspond to physical database tables, field objects may correspond to physical columns in a database table, and meta-relations 120 may correspond to foreign keys used to reference field objects and meta-tables. In other cases, objects within the metabase 26 do not exist in their own right within a physical database, but may be treated as objects by the metabase 26.

Figure 2:
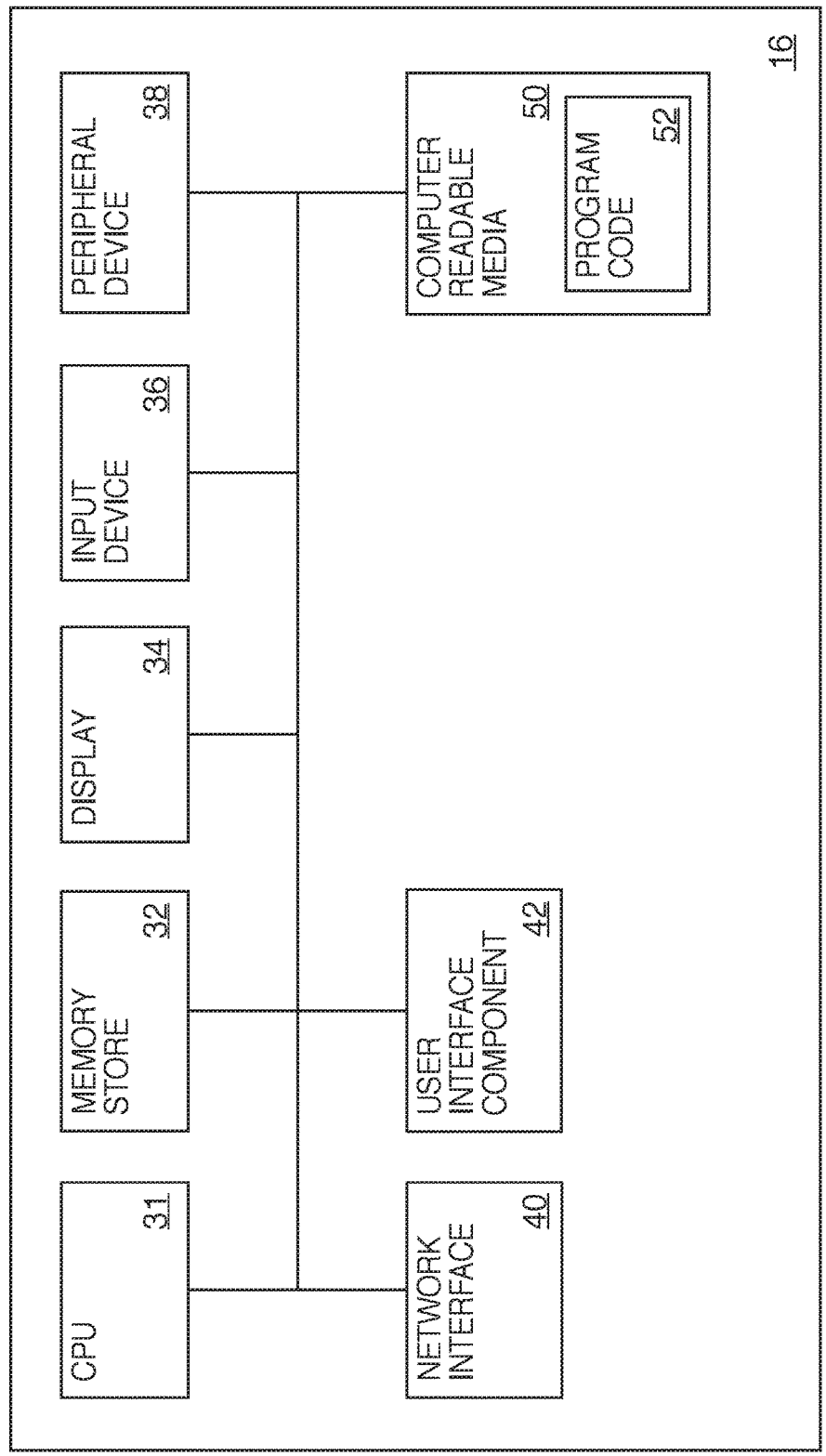
FIG. 2 is a block diagram illustrating the components of an administrative workstation of a system for creating a form for receiving data in accordance with an example embodiment.

FIG. 2 is a block diagram illustrating the components of a workstation 16 of a system 10 for creating a form for receiving data in accordance with an example embodiment.

Workstation 16 may be any networked computing device including a processor and memory, such as a personal computer, workstation, server, portable computer, mobile phone, personal digital assistant, laptop, smart phone, satellite phone, WAP phone, or a combination of these. Workstation 16 may include a software application, application plug-in (e.g. a widget), instant messaging application, mobile device application, e-mail application, online telephony application, java application, web page, or web object (e.g. a widget) residing or rendered on workstation 16 in order to access data system 12 using network 16. Furthermore, any user of health care incident management system 12, such as an administrator, a doctor, a nurse, or any other user, may access workstation 16.

In an exemplary embodiment, workstation 16 includes a central processing unit 31, a memory store 32, a display 34, an input device 36, one or more peripheral devices 38, a network interface 40 and a computer readable media 50. Workstation may also include a user interface component 42, or alternatively may access interface module 24 of health care incident management system 12 via network 14. The functionality of user interface module 42 is the same as described in relation to interface module 24.

The display 34 is a monitor type device that is used to display information. The input devices 36 may be any device that allows for input, examples of which may include, but are not limited to, keyboards, touch screens, microphones, speakers, and pointing devices. The memory store 32 is a permanent storage associated with the device. The central processing unit 31 is used to execute instructions or program code 52 stored on computer readable media 50 or memory store 32. The program code 52 on computer readable media 50 may be stored on memory store 32. The network interface 40 may be a wired and/or wireless network interface that allows the device to connect to the network 14. The peripheral devices 38 may include but are not limited to, devices such as printers, antenna, transceivers and scanners.

User interface component 42 is operable to provide a user interface on display 34 for creating user-defined field objects, creating forms, and generating reports by a user of the workstation 16. In some embodiments, user interface component 42 is operable to relay information from interface module 24 in health care incident management system 12. Although user interface component 42 is shown to reside on workstation 16, the user interface component 24 may reside on a web server (not shown) or in data system 12, as a component of interface module 24, and accessible to workstation 16 via network 14. Accordingly, the terms user interface component 42 and interface module 24 may be used interchangeably herein.

User interface component 42 receives instructions to create user-defined field objects and forms or generate reports via input device 36. The user interface component 42 communicates with health care incident management system 12 over network interface 14 to generate forms and reports using form engine 20 and report engine 22 residing in health care incident management system 12. The user interface component 42 provides the returned forms and reports on display 34. Once a user has entered field values into a form, user interface component 42 is operable to store the received field values within metabase 26. Persistent store 30 is operable to store the field values, with metabase tables 28 maintaining the location and the relationships between the user, the field values, and the forms.

Figure 3A:
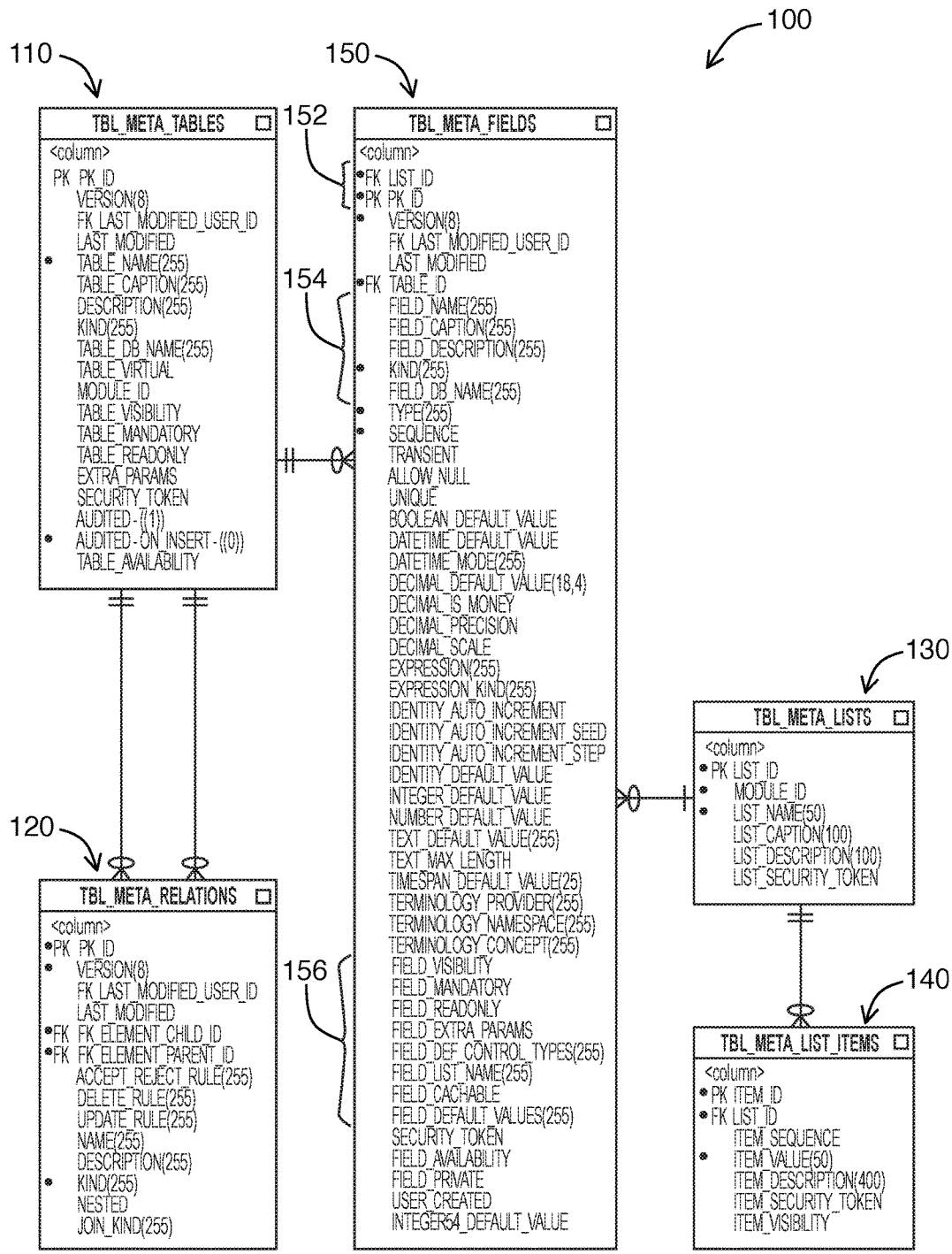
FIG. 3A is a schema diagram of a metabase for storing data related to a form in accordance with an example embodiment.

FIG. 3A is a schema diagram 100 of an exemplary metabase 26 for storing data related to a form in accordance with an example embodiment. Metabase 26 contains a dictionary of field objects. In some embodiments, a metabase 26 may contain more than one dictionary. For example, a metabase may have different dictionaries for storing forms as field objects. A field object is stored in metabase 26 in both metabase tables 28 and persistent store 30. Metabase 26 also defines how different field objects relate to other field objects. For example, metabase 26 may describe how a field object, corresponding to a person, relates to a field object corresponding to a hospital admissions incident. Metabase 26 is flexible and is further operable to store information relating a person to every admission into the hospital.

In the exemplary schema diagram 100 metadata 150 is stored in metabase tables 28 in one or more tables. Metadata 150 regarding a field object is stored in TBL_META-_FIELDS. In some embodiments, the metabase 26 is configured to store presentation attributes 156 relating to how an instance of the field object will be presented in a form field and how it may behave. Presentation attributes may include conditional visibility, type of input control (e.g., a text box, radio buttons, a list, a dropdown list, checkboxes), format of input, dimensions of the form field validation rules, and the like.

Metadata 150 may store additional attributes and relationships in additional metabase tables 28. For example, metadata 150 may use primary and foreign keys 152 to link attributes relating to a field object to meta-lists 130 and meta-list items 140. Meta-list 130 may store potential field values for a field object. For example, if the field object relates to "Province", then the meta-list may store potential fields values "Ontario", "British Columbia" and "Quebec", for example. Meta-list items 140 may store attributes pertaining to a potential field value. For example, a meta-list item may store sequence information for a potential field value within the meta-list 130.

Metadata 150 may also store relational information in metabase tables 28. Meta-table 110 may store a list of related field objects. Furthermore, meta-relations 120 may store the type of relationships between related field objects and its related field objects for each related field object or between related meta-tables 110. For example, a field object corresponding to a person may be related to a name and an address. Similarly, a field object relating to a doctor may be related to a person. In some embodiments, metabase 26 may structure the dictionary of field objects (in corresponding meta-tables 110) into parent-child relationships to arrange the field objects into a tree. Each node of the tree may correspond to one or more field objects. Furthermore, a field object or meta-table 110 may have one or more parent nodes and one or more child nodes maintained by meta-relations 120. A meta-table 110 that does not have a parent may be considered a root metatable. In health care incident management system 12, a root meta-table may include: an incident report, a patient feedback report, claims for damages, infection cases, and the like.

Figure 3B:
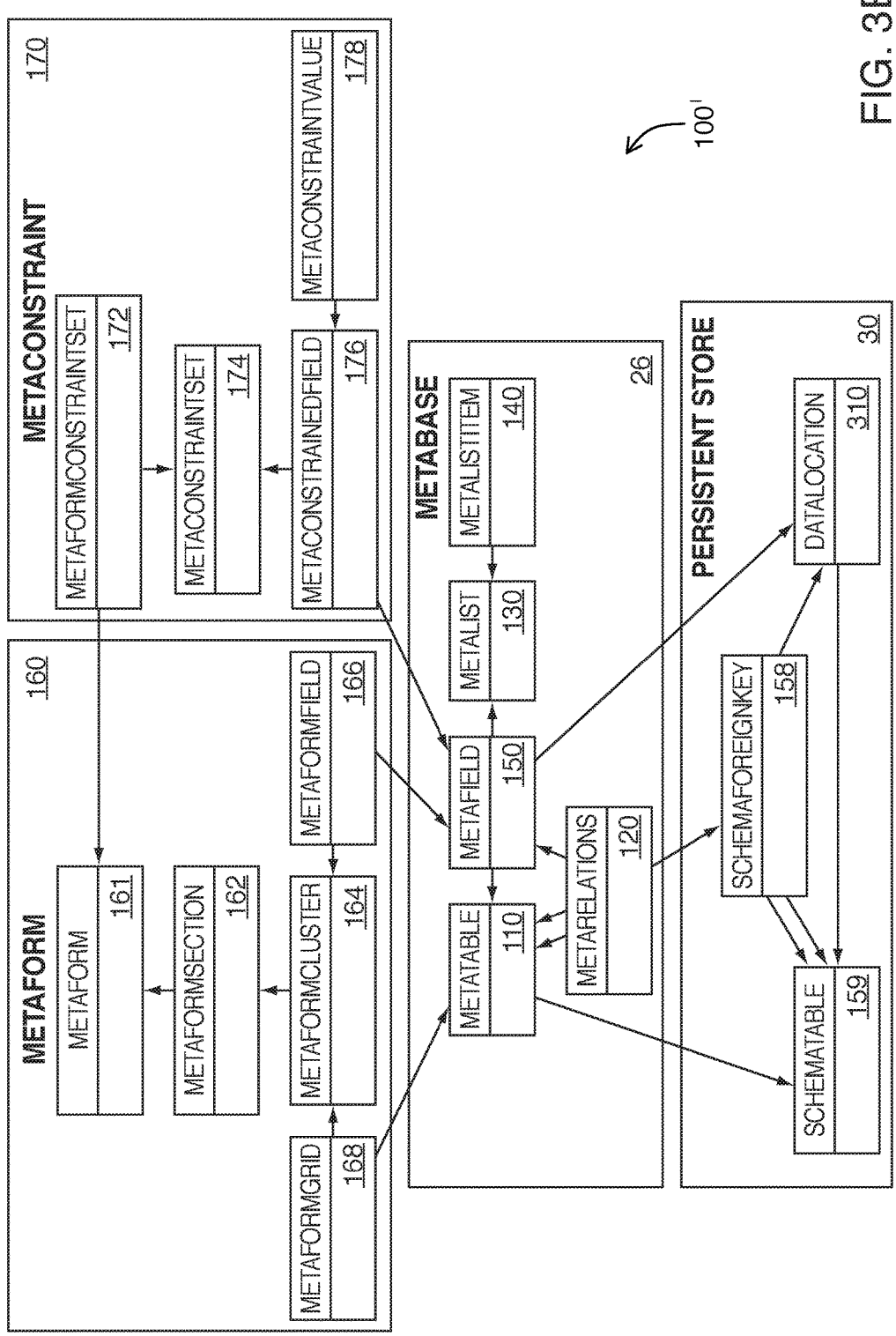
FIG. 3B is a schema diagram of a health care incident management system in accordance with an example embodiment.

FIG. 3B is a schema diagram 100' of a health care incident management system 12 in accordance with an example embodiment. Similar to the schema diagram 100 in FIG. 3A, metabase 26 is illustrated as a number of tables linked by primary and foreign keys 152. FIG. 3B may expand on the schema diagram 100 in FIG. 3A by providing a higher-level view of the metabase 26, including interconnections to objects in the metaform 160, the metaconstraint 170, and the persistent store 30. Whereas FIG. 3A may illustrate the physical implementation of a metabase 26 in an example embodiment, schema diagram 100' may illustrate incorporating the metabase 26 into the health care incident management system 12 to provide field objects, forms, and storage. Form engine 20 is operable to use metaform 160 and metaconstraint 170 to generate forms.

With reference to the schema diagram 100' in FIG. 3B, the persistent store 30 is operable to store a schemaforeignkey 158 and a schematable 159. In some embodiments, the metabase 26 may use the schemaforeignkey 158 to reference a record in the schematable 159 in order to find the field value of a particular field object in a referenced data location 310. The data location 310 may be a column in the schematable 159.

Metaform 160 is operable to store the structure of the forms as will be described herein. When form engine 20 accesses metabase 26 to generate a form, form engine 20 may access the form objects stored within the metaform 160 to define how the form will be ordered for the user. For example, a form object may include the form 161, one or more form sections stored in a metaformsection 162, one or more form clusters stored as a metaformcluster 164, and one or more form fields (which are instances of field objects) stored as a metaformfield 166. Furthermore, the metaform 160 may include a form grid 168 as a special instance of a form cluster 164. In at least one embodiment, the relationships between the different form objects stored in the metaform 160 may be structured according to the schema diagram 100' as will be further discussed herein.

Metaconstraint 170 is operable to store the structure of constraint sets as will be described herein. Briefly, metaconstraint 170 may include a metaformconstraintset 172, a metaconstraintset 174, and metaconstrainedfield 176 and a metaconstraintvalue 178. Form engine 20 is operable to utilize these objects to generate a set of field value constraints for a set of form fields within a form. Specifically, form engine 20 may utilize the information stored within a metaconstraint 170 to modify the behavior of related field objects such that in certain circumstances lists of selectable field values will be constrained to reflect previous selections. As will be appreciated by those skilled in the art, the data and data structures shown in FIG. 3A and FIG. 3B are provided for exemplary purposes only and are not to be construed as limiting. Variations to the types of data stored and the organizational structures, lists and tables used to store information using metabase 26 and metatables 28 are possible in alternative embodiments.

Figure 4:
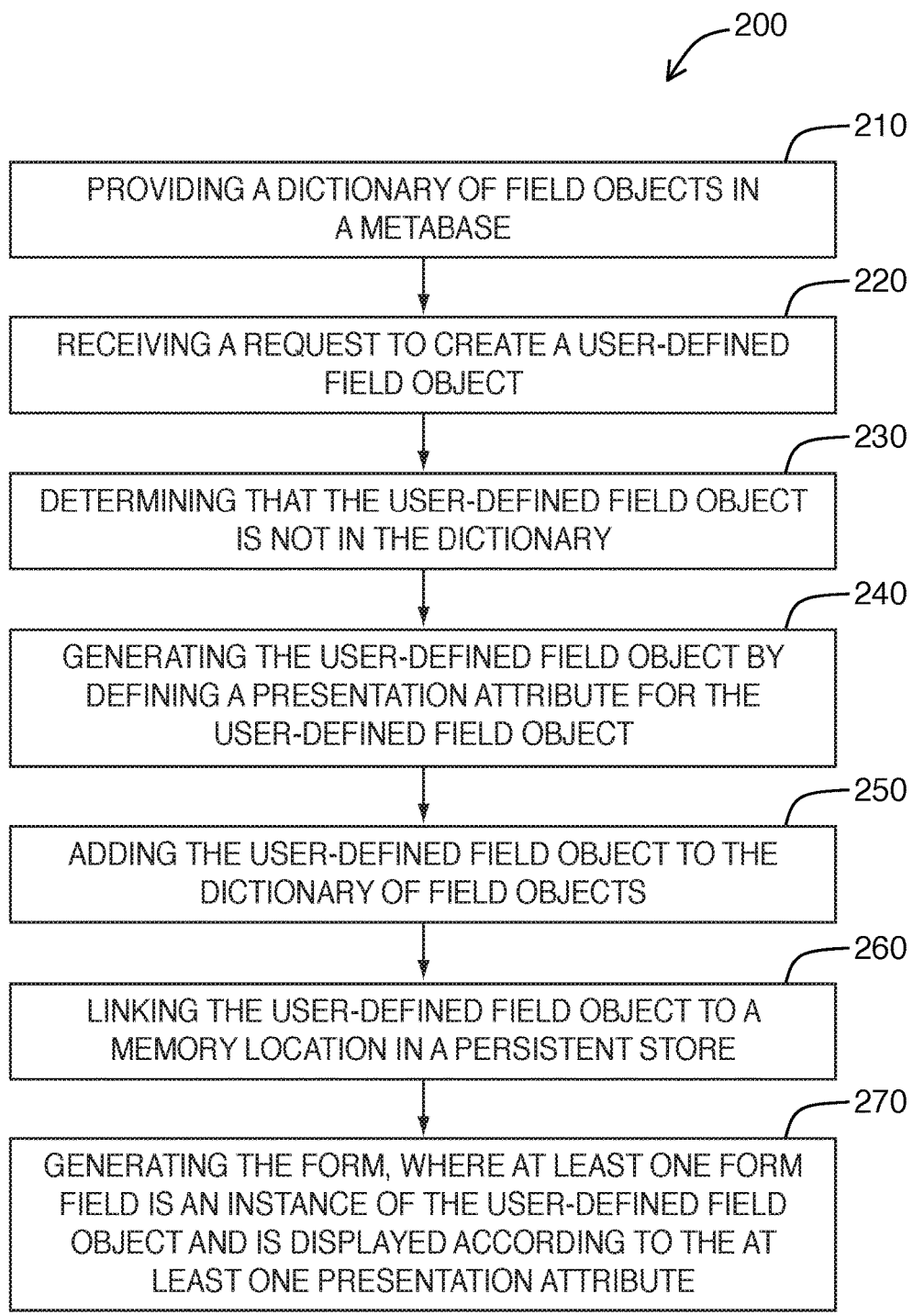
FIG. 4 is a flow diagram of a method for creating a form for receiving data in accordance with an example embodiment.

FIG. 4 is a flow diagram 200 for creating a form for receiving data in accordance with an example embodiment. Health care incident management system 12 is operable to create a user-defined field object that is not already in its dictionary of field objects. Creating user-defined field objects may provide flexibility and customization over a database system based on a static set of data fields or fixed field database where an administrative user is limited to re-tasking the pre-defined fields.

In some embodiments, user-defined field objects may be configured to operate similar to pre-defined field objects. Health care incident management system 12 is further operable to use user-defined field objects to extend or entirely replace a predefined database schema. As the field of healthcare risk management matures, more formal incident taxonomies are evolving. Notable examples have been published by the Agency for Healthcare Research and Quality in the United States and the World Health Organization. Health care incident management system 12 implements user-defined field objects to provide a flexible metaschema which allows a new taxonomy to be adopted, and ongoing taxonomic changes to be accommodated, without modifications to applications that depend on the metabase 26. Instead, health care incident management system 12 generates user-defined field objects to represent the new or modified taxonomy.

The process of creating a form starts at step (210), where health care incident management system 12 provides a dictionary of field objects in a metabase 26. For example, a field object may be a person, a doctor, a person's name, or a doctor's name. Each field object may define one or more relationships. Furthermore, each field object defines one or more attributes. Data system 12 stores these attributes and relationships with the field object in metabase 26 using metabase tables 28.

An administrator creating a form may be situated at workstation 16 using an administrator application. The administrator application is operable to access user interface component 42 to create new forms. Forms are ordered collections of form fields and an administrator selects the field objects that are to be included in a form. A form field selected to be in a form is considered an instance of a field object. If a desired field object is not present in the dictionary of field objects, an administrator may decide to create a user-defined field object.

In step (220), user interface component 42 is operable to receive a request to create a user-defined field object. For example, a user-defined field object defines a new type of equipment purchased by a health care facility, or to define a replacement date for current equipment. In another example, a user-defined field object defines a new facility or a new ward that is opening within a hospital.

In step (230), data system 12 determines that the user-defined field object is not in the dictionary of field objects. Data system 12 is operable to search metabase to determine whether a specific field object is in the dictionary of field objects. Metabase 26 may be operable to search a list of field objects prior to creating a user-defined field object to detect if the name is already in use.

In step (240), the user-defined field object is generated by defining attributes. The attributes may be stored as metadata within metabase tables 28 and may define how the field object is stored within metabase 26. As discussed, the attributes may also define the relationship between the field object and other field objects, users, and forms. An attribute may also define the type of input data that a form field (which is an instance of the field object) may receive, how the input data may be structured and/or formatted and the like.

Figure 5:
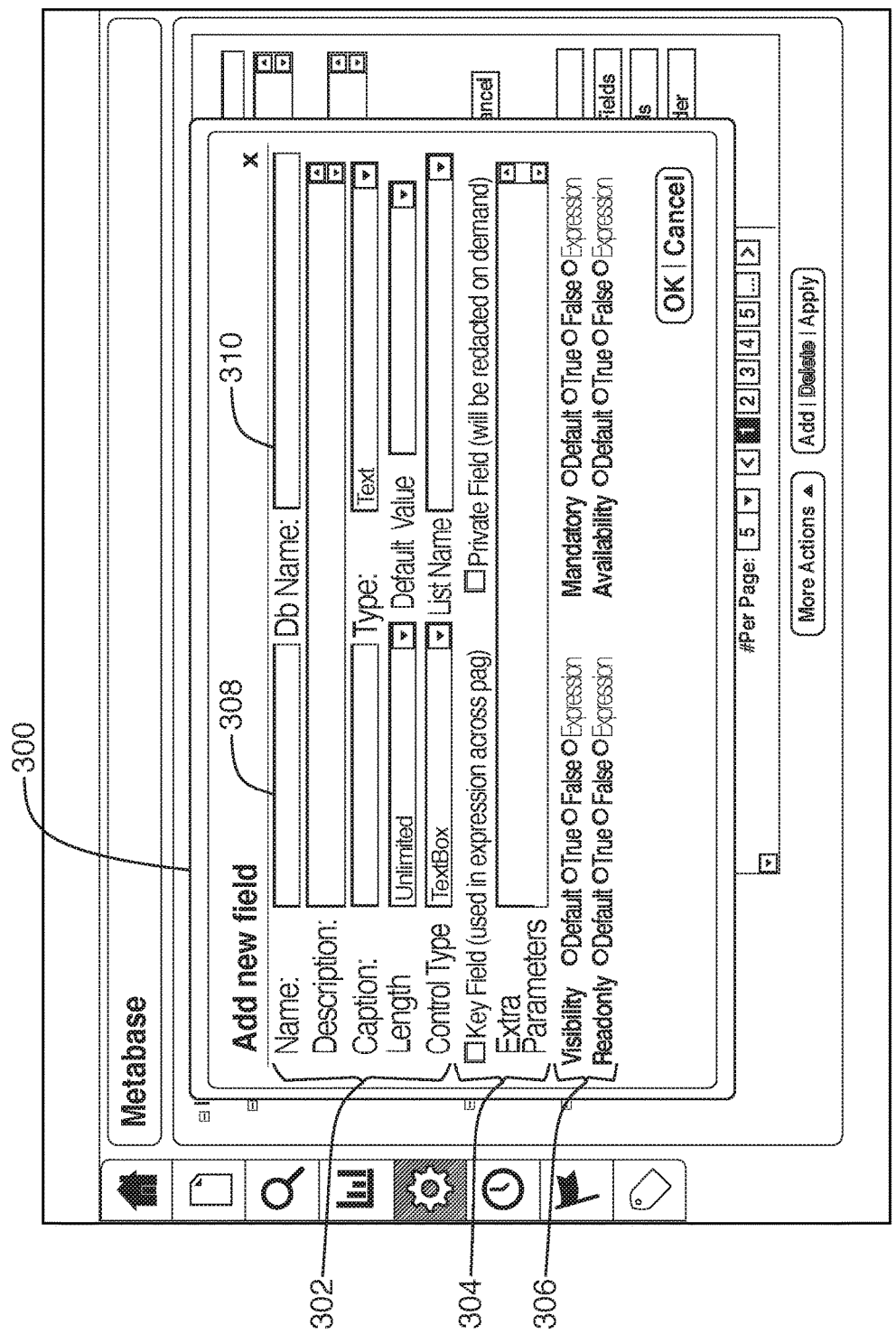
FIG. 5 is a screen shot diagram of a user interface component for defining attributes corresponding to a user-defined field object in accordance with an example embodiment.

FIG. 5 is a screen shot diagram of a user interface component 42 for defining attributes corresponding to a user-defined field object in accordance with an example embodiment. The user interface component 42, such as dialog box 300, may provide a set of selectable attributes. The attributes may be related to where the data is stored and how the field value is received within a form field. For example, the name 308 of the field object may be stored and a corresponding data location 310 within the persistent store 30 may be identified or created. If the user-defined field object being created has no corresponding data location within the persistent store 30, a new column in the persistent store may be created for the field object. The metabase then stores a link to the column or data location within the attributes of the user-defined field object.

The attributes are stored within metabase 26 and allow health care incident management system 12 to abstract the structure and metadata of the field objects from the corresponding field values stored in the persistent store 30. A form field is an instance of the field object and can be labeled with any name, wherein the name is stored as an attribute. The attributes may be presentation attributes 306 and control whether a form field, as an instance of the field object is mandatory, read-only, visible, or available. Presentation attributes 306 may also include a field caption, the type of control the form field will assume, or whether there is a default value for the form field. For example, control types may include a text box, a date box, a time box, a list, a boolean checkbox, a number box, radio buttons, and the like.

Health care incident management system 12 is operable to define a field object by defining a number of attributes for the field object. Health care incident management system 12 is operable to store the attributes in metabase tables 28 within the metabase 26. For example, a table of exemplary attributes is described below:

| Attribute | Description |
| --- | --- |
| Primary Key Identifier | The attribute may identify a field definition or act as an internal identifier. |
| Version | The attribute may store the current version of the field definition. |
| Last User to Modify | The attribute may identify the user who most recently modified the field definition. |
| Time of Last Modification | The attribute may timestamp the most recent modification. |
| Table Identifier | The attribute may identify the meta table to which the field belongs. |
| Field Name | The attribute may identify the field name to the end user, i.e., the administrator. |
| Field Caption | The field caption may provide the user interface caption. |
| Field Description | The field description may provide an explanation of how the field is to be used. It may be available to the end user. |
| Kind | The attribute may distinguish fields that contain business information from fields that contain system information. |

-continued

| Attribute | Description |
| --- | --- |
| Database Field Name | The attribute may store the name of the physical database column to which the field is bound. |
| Type | The field type is the logical data type of the field. |
| Sequence | The sequence may be used for ordering the field in the user interface. |
| Transient | The transient attribute may indicate whether the field is persistent or transient. |
| Allow Null | The attribute may indicate whether the field allows NULL values. |
| Unique | The attribute may indicate whether the field's value must be unique. |
| Boolean Default Value | The attribute may store the default value if the field's type is Boolean. |
| Datetime Default Value | The attribute may store the default value if the field's type is datetime. |
| Datetime Mode | The attribute may control the mode of the datetime field. |
| Decimal Default Value | The attribute may store the default value if the field type is a decimal. |
| Decimal Is Money | The attribute may indicate that the decimal field contains a money value. |
| Decimal Precision | The attribute may store the number of digits after a decimal, for a decimal field. |
| Decimal Scale | The attribute may store the total number of digits for a decimal field. |
| Expression | The attribute may store an expression used to compute the field default value. |
| Kind Of Expression | The attribute may store the type of expression used to compute the default value. |
| Identity Auto Increment | The attribute may store an indication that the field is an auto-generated identifier. |
| Identity Auto Increment Seed | The attribute may store a seed value for an auto-generated identifier. |
| Identity Auto Increment Step | The attribute may store a step value for an auto-generated identifier. |
| Identity Default Value | The attribute may store a starting value for an auto-generated identifier. |
| Integer Default Value | The attribute may store a default value if the field type is an integer. |
| Number Default Value | The attribute may store a default value if the field type is a number. |
| Text Default Value | The attribute may store a default value if the field type is text. |
| Maximum Length Of Text | The attribute may store a maximum number of characters allowed in a text field. |
| Timespan Default Value | The attribute may store a default value if the field type is a timespan. |
| Terminology Provider | The attribute may store an optional data source for field values. |
| Terminology Namespace | The attribute may store an optional classification for a terminology provider. |
| Terminology Concept | The attribute may store an optional sub-classification for a terminology provider. |
| Mandatory | The attribute may store an expression determining if the field is visible to the end user. |
| Read-Only | The attribute may store an expression determining if the field is mandatory for the end user. |
| Visible | The attribute may store an expression determining if the field is modifiable by the end user. |
| Extra Parameters | The attribute may store additional field-type specific parameters. |
| List Name | The attribute may store a name of a pick list associated with the field. |
| Cachable | The attribute may indicate that the field may be cached in memory at runtime. |
| Default Value | The attribute may store a generic default value for the field. |
| Security Token | The attribute may control administrator access to the configuration of the field. |
| Availability | The attribute may store an expression determining if the field may have a value. |
| Control Type | The attribute may store a user interface control type used for the field. |
| Private | The attribute may store a flag indicating that the field is to be redacted by a redaction process. |
| User Created | The attribute may store a flag indicating the field is not part of the core field set. |
| Identity Use Int64 | The attribute may store a flag indicating that if the field is an identity, it is a 64-bit identity. |
| Inter Default Value | The attribute may store a default value if the field type is bigint. |
| Verification Mask | The attribute may store a mask limiting the format of a received input. |

It should be understood that the attributes mentioned in the above table are examples only. Other attributes are also possible for defining field objects in alternative embodiments. The attributes described above should not be construed as limiting.

Health care incident management system 12 is operable to create separate field objects using the same underlying field value. Separate field objects in metabase 26 referring to the same underlying field value in persistent store 30 may be defined with different attributes. For example, two field objects referring to the same underlying field value may have different caption attributes. This may be beneficial where different users within health care incident management system 12 refer to the same field value by different names. For example, a date form field for reporting when an incident occurred may, in some applications, be captioned "Date of Incident". However, in some forms, it may be desired to caption the same underlying field value, "Date of Fall Incident" or "Discovery Date of Incident". Metabase 26 is operable to provide this flexibility by abstracting from the underlying field value in persistent store 30. Caption information may be stored as an attribute to the field object in metabase tables 28.

An additional benefit of abstraction using metabase 26 is that two field objects with the same underlying field value may have different presentation attributes 306. Accordingly, health care incident management system 12 may create field objects that are presented for different purposes. In some forms, health care incident management system 12 may present a field object incorporating a drop down list. In another form, a health care incident management system 12 may present a different field object corresponding to the same underlying field value using radio buttons. Creating separate field objects for the same underlying field value increases the flexibility of health care incident management system 12 and allows custom forms to include custom form fields to improve form design and workflow.

Depending on the type of control, the form field may have additional attributes 302, 304, 306. For example, if the form field is a text box for receiving a field value related to an email address, the field object may have a verification mask to confirm that the field value received matches with a format or within parameters expected of the field object.

User interface component 42 may receive a selected attribute for defining a user-defined field object in a dialog box 300. Once selected, the health care incident management system 12 may define the selected attribute as an attribute for the user-defined field object. User interface component 42 may save the selected attribute in memory store 32 or provide the selected attribute to data system 12. Data system 12 saves the attribute in the metabase 26 as part of the user-defined field object.

In some embodiments, the user interface component 42 may facilitate the creation of a new user-defined field object by providing suggestions for attributes and attribute values. For example, health care incident management system 12 may allow a user to replicate a field object (i.e. copy a field object's attributes) for use in a different purpose. In another example, certain types of attribute fields within the user interface component 42 may provide a selection of attribute values for an administrator to choose from.

Figure 6:
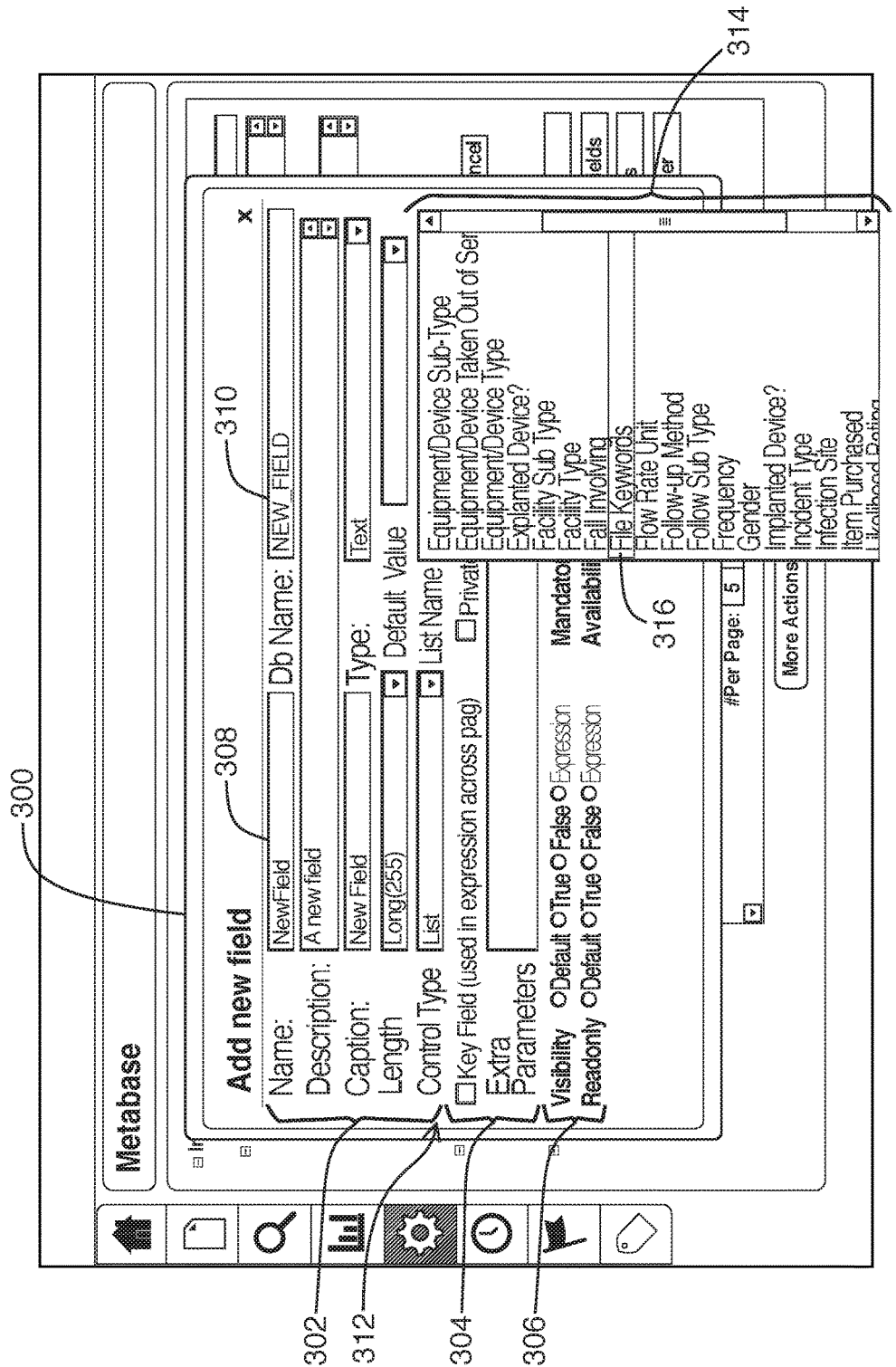
FIG. 6 is a screen shot diagram of a user interface component for defining attributes corresponding to a user-defined field object from a set of selectable attribute values in accordance with an example embodiment.

FIG. 6 is a screen shot diagram of a user interface component 42 for defining attributes corresponding to a user-defined field object from a set of selectable attribute values in accordance with an example embodiment. For example, if the control type 312 is a list control type then a drop down list 314 may be provided with a set of selectable attribute values based on the selected attribute. In this case, a drop down list 314 of different list names is provided on display 34. The user interface component 42 is operable to receive a selected attribute value 316 from the drop down list 314. It is then operable to link the selected attribute value 316 to the selected attribute linked to the user-defined field object.

In the example embodiment illustrated in FIG. 6, user interface component 42 receives a selected attribute called "List Name" and the selected attribute value 316 named "File Keywords". The selected attribute value may be selected from a group of potential attribute values determined by health care incident management system 12 or, in this example, reference a table of list items defined by meta-list 130 and stored within metabase 26 to include in the form field instance of the field object. The set of potential attribute values may be provided in a drop down list 314.

In step (250), the user-defined field object is added to the dictionary. This may include adding the user-defined field object to the dictionary of field objects in metabase 26. Attributes corresponding to the user-defined field object are stored in metabase tables 28. In some embodiments, data system 12 may associate an attribute with a user-defined field object to identify the field object as user-defined and not originally provided in the dictionary of field objects.

In step (260), the user-defined field object is linked to a data location 310 in persistent store 30. The data location may reference a column in persistent store 30. Metabase 26 is operable to create a new column in persistent store 30 when a new user-defined field object is created. The tables in persistent store 30 may not be initially created larger to accommodate future field objects. Rather, the number of columns in persistent store 30 is dynamic according to the number of field objects in the dictionary within the metabase 26. Accordingly, persistent store 30 may operate more efficiently and may require less storage to accommodate the set of field objects in the dictionary.

In step (270), the form is generated using form engine 20. The form is comprised of an ordered collection of form fields. Form engine 20 is operable to retrieve the corresponding field objects from the metabase 26 and use the attributes defining the field object to create a form field. The form field may be an instance of a user-defined field object and furthermore, may be displayed according to a presentation attribute. The form field may be configured to receive field data relating to a health care incident.

Health care incident management system 12 may provide a form on workstation 16 for access by a user. The workstation is operable to submit a request for a particular form to health care incident management system 12 via network 14. Form engine 20 is operable to process the request and return a generated form to the user for entering input data.

Once the form is generated, workstation 16 displays the form on display 34 and receives field values from the different form fields. A form field within the form may be an instance of a user-defined field object. When placed in a form, the form field is configured to receive input data related to the user-defined field object.

In some embodiments, interface module 24 is operable to limit the format of the received input data. For example, the form field may be limited to accepting only numbers for field objects defined as integer field objects. Similarly, a form field may use a verification mask to ensure the input data meets the desired requirements, such as for an email address. A field object is operable to store a verification mask as an attribute in the metabase 26.

Figure 7:
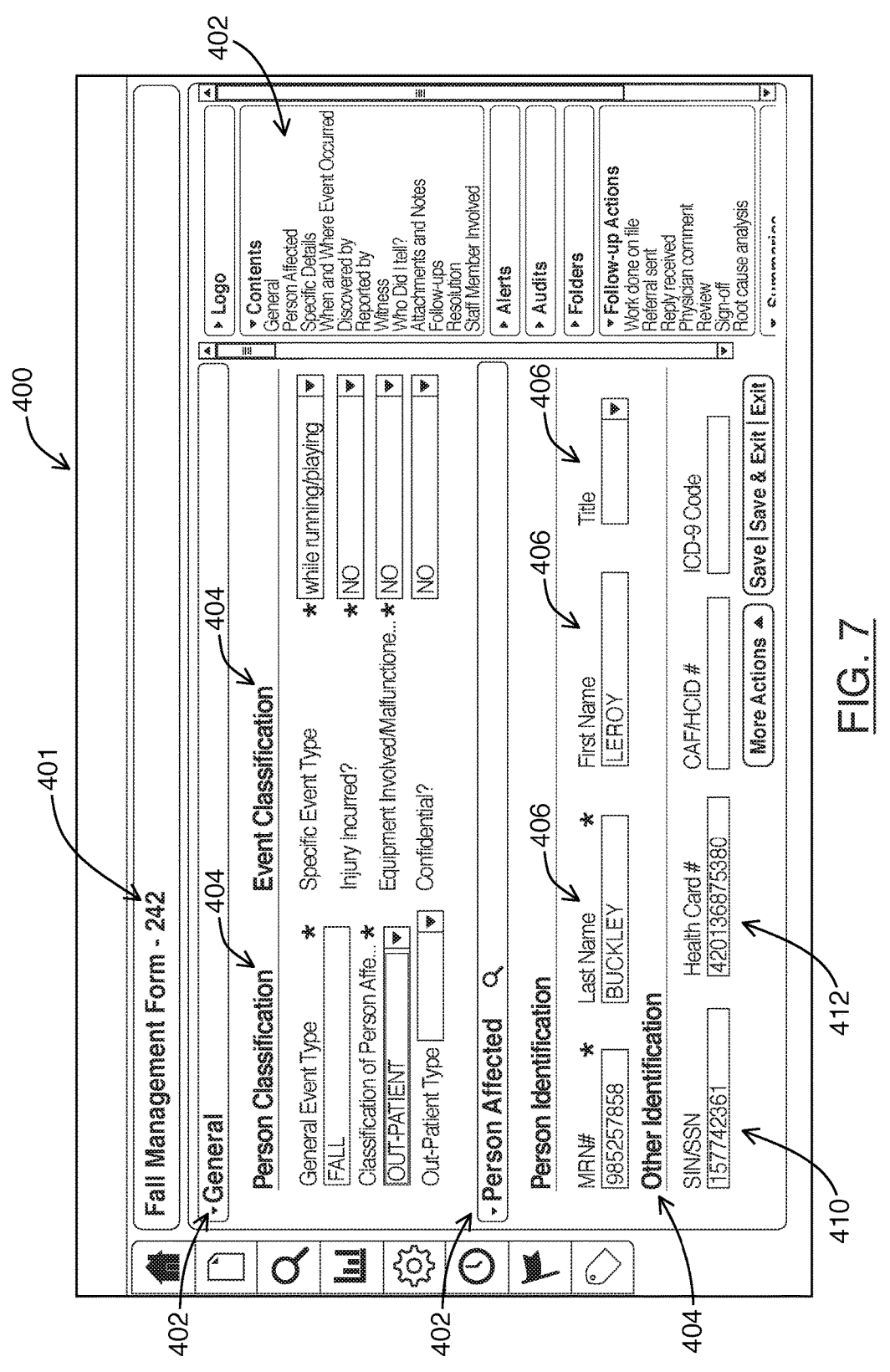

FIG. 7 is a screen shot diagram of a form in accordance with an example embodiment. A form 400 may be organized into clusters 404 and sections 402. A cluster 404 may be regarded as a group of form fields 406. Often, the form fields 406 may be organized for specific purpose. For example, a cluster 404 may be for a group of form fields related to an address (e.g. number, street, city, country) or a piece of equipment (e.g. name, style, model number). Each form field may be an instance of a different field object.

In the exemplary form 400 illustrated in FIG. 7, form fields 406 are grouped in clusters 404 labeled "Person Classification" and "Event Classification". A section 402 may be regarded as a group of clusters 404. For example, a section 402 labeled "Person Affected" may include clusters 404 related to "Person Identification" and "Other Identification". In example form 400 related to "Fall Management", sections 402 may include "Specific Event Details" and "Witness". Furthermore, sections 402 may be collapsible (not shown) within a form 400 to allow a user easy navigation to the different sections 402, clusters 404 and form fields 406 within a form 400.

In some embodiments, metabase 26 is operable to store a form 400. The form 400, sections 402, clusters 404, and form fields 406 are considered field objects. The form may be related to sections 402, which in turn may be related to clusters 404. Clusters 404 may be related to the component form fields 406. The flexibility of this data structure for forms within metabase 26 allows clusters 404 and sections 402 to be copied and reused in different forms. Furthermore, forms 400 may have their own internal structure—i.e., sections 402 and clusters 404, that determine the position and order of form fields as presented to the end user.

In some embodiments, metabase 26 is operable to store a form as a collection of field objects. Health care incident management system 12 may be configured to arrange the dictionary of field objects in the metabase 26 as a tree of nodes. Each node is operable to create relations to one or more parent nodes and one or more child nodes. Each node is comprised of a field object and may be defined by one or more attributes.

Metabase 26 is operable to associate a field object with one or more forms. The field object may be a user-defined field object. In some embodiments, if a form field corresponding to a parent node is added to a form, additional form fields associated with one or more children of the parent node will be added to the form.

Metabase 26 is operable to determine that a generated form comprises a form field corresponding to a parent node. The form field may be an instance of the user-defined field object. Metabase 26 may refer to the tree of nodes to add additional form fields. Additional form fields may correspond to one or more child nodes of the parent node. These additional form fields may be added to the form automatically.

For example, an administrator may access health care incident management system 12 to create a form using workstation 16. By adding a form field to a form, interface module 24 may recognize the field object as a parent node. As an example, a user may add a form field as an instance of a field object related to a piece of equipment involved in an incident. When the form field is added, metabase 26 may determine that additional form fields related to the equipment involved should also be added to the form. Additional form fields may include the equipment supply type, the equipment manufacturer, the equipment serial number and the like. As the form field related to the piece of equipment involved is stored in a parent node in a tree of nodes and the equipment supply type, the equipment manufacture and the equipment serial number are stored as children, metabase 26 is operable to refer to children of the parent to determine what additional form fields to add to the form.

In some embodiments, form engine 20 is operable to add additional form fields to the form as a cluster associated with the form field corresponding to the parent node. The additional form fields may be available to receive field values whenever the form field corresponding to the parent node is available. In alternative embodiments, form engine 20 is operable to operate a dialog box to collect field values corresponding to the child nodes. In the example relating to equipment involved in an incident, a dialog box may appear when a user activates the form field corresponding to the parent node. The dialog box is then operable to collect field values corresponding to the field objects of the child nodes.

In some embodiments, the health care incident management system 12 may implement security features to limit the types of forms and field objects within forms that are not permitted to be displayed for certain user identifiers. Health care incident management system 12 provides this flexible access control using attribute values stored in association with the field objects. The attributes and field objects are arranged within the dictionary stored in metabase 26.

Metabase 26 is operable to provide multiple layers of security for forms and reports. Security may be provided on a role level, on a form level or on a field level. The security methods may be tied to specific field objects by defining security attributes. Each user, identified by a user identifier, is configured with security and access parameters according to their role and data scope.

Health care incident management system 12 is operable to limit access to forms and reports according to the role of the user identifier. For example, doctors, nurses, and incident managers may have different roles within the incident management process. Accordingly, a system administrator may provide different access privileges to the different roles. For examples, while nurses may be able to access forms related to incidents, they may not have privileges to access follow-up forms related to those incident forms.

In some embodiments, a user identifier may have access to a form in certain roles, but may be excluded from corresponding reports. In further embodiments, data access may be on an individual user level. In some embodiments, health care incident management system 12 is operable to exclude a user identifier from certain reports except where the user identifier has created the underlying field data.

Health care incident management system 12 is operable to limit access to forms and reports according to the data scope of different user identifiers. Different user identifiers may have different access privileges according to their data scope. For example, a doctor within one section of a hospital may be excluded from accessing patient or incident reports created in a separate section of the hospital. Further, the data scope may limit access on a form or a field level. In one example, a doctor may be excluded from accessing forms or reports where a patient has submitted a claim against the doctor. In another example, forms where a field object indicates a patient has died may have increased access restrictions.

Access control over a form and form fields may be determined when health care incident management system 12 receives a request to generate the form, and the request includes a user identifier. The user identifier will be appended with a request or query for a form and sent to health care incident management system 12. The user identifier is associated with a user role. The user role defines a data scope and the data scope ultimately defines a set of permitted form fields. In some embodiments, the data scope will define a set of fields forbidden to the user identifier.

Upon receipt of a request for a form, health care incident management system 12 will determine if the request to generate the form is a permitted search request. Health care incident management system 12 may refer to a user role and data scope to make this determination. Metabase 26 is operable to store user roles and data scopes associated with user identifiers. A user role may include the user identifier's position within health care incident management system 12, i.e., a manager, a doctor, or a nurse. Certain user roles may be assigned different access rights. A user identifier may also have different data scopes that grant different privileges on a form field level. Health care incident management system 12 is operable to determine that the request to generate the form is a permitted search request according to the data scope associated with the user identifier.

In some situations specific form fields may be outside a user identifier's scope. For example, a manager may have additional fields in a form to indicate what further actions need to be taken. These form fields may be unavailable to a front line worker, such as a nurse or a doctor. Accordingly, form engine 20 may receive a request for the same form from different user identifiers but in response may return the same form with different form fields. Form engine 20 may limit the collection of form fields in a form according to the data scope associated with the requesting user identifier. Form engine 20 is operable to generate the report using the plurality of field objects and exclude data corresponding to the one or more field objects forbidden to the user identifier.

Figure 8:
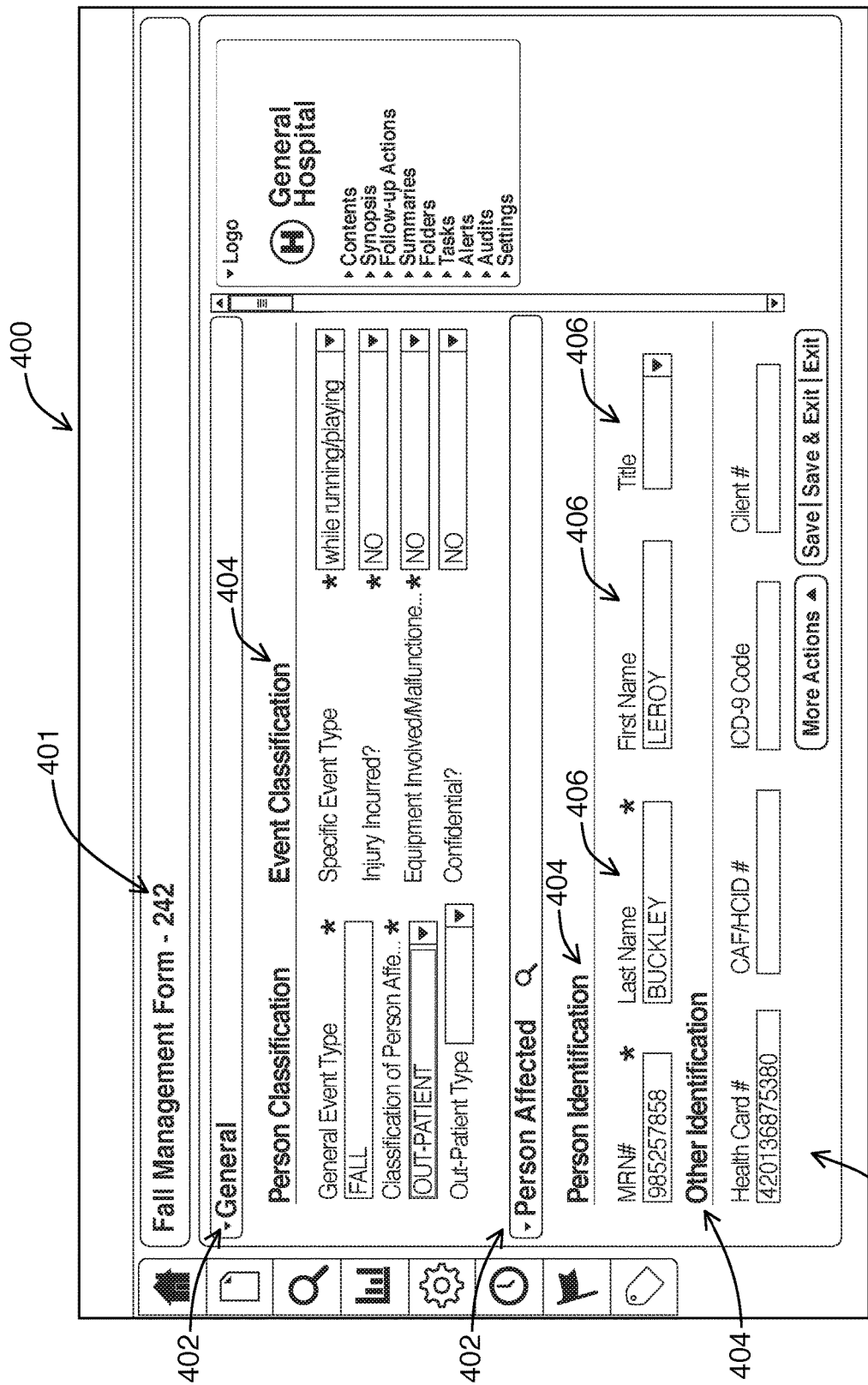
FIG. 8 is a screen shot diagram of a form with a forbidden form field withheld from the form in accordance with an example embodiment.

FIG. 8 is a screen shot diagram of a form with a forbidden form field withheld from the form in accordance with an example embodiment. The form 400 is similar to form 400 seen in FIG. 7 but was requested by a different user identifier. For example, exemplary form 400 is a "Fall Management Form—242" with the same form identifier 401 in FIG. 7 and FIG. 8. The users may have different user roles or data scope within health care incident management system 12. Accordingly, in comparison to the form 400 of FIG. 7, the user identifier in FIG. 8 is missing a form field corresponding to SIN/SSN 410 available to the user identifier in FIG. 7. In some embodiments, the form engine 20 may be operable to provide a form 400 to the user identifier in FIG. 8 that does not indicate certain form fields are forbidden. The user associated with the user identifier may be unaware that certain form fields are withheld. In FIG. 8, the form fields have shifted over to replace the space taken by the field related to SIN/SSN 410. In its place is a form field related to a Health Card #412.

To determine which form fields are to be included in a form, the health care incident management system 12 may provide a form designer through interface module 24. The form designer may allow an administrator to design and create new forms using the field objects stored within metabase 26. An administrator may further save the created forms within metabase 26. The form may be generated with form engine 20 and accessed via workstations 16 over network 14.

Figure 9:
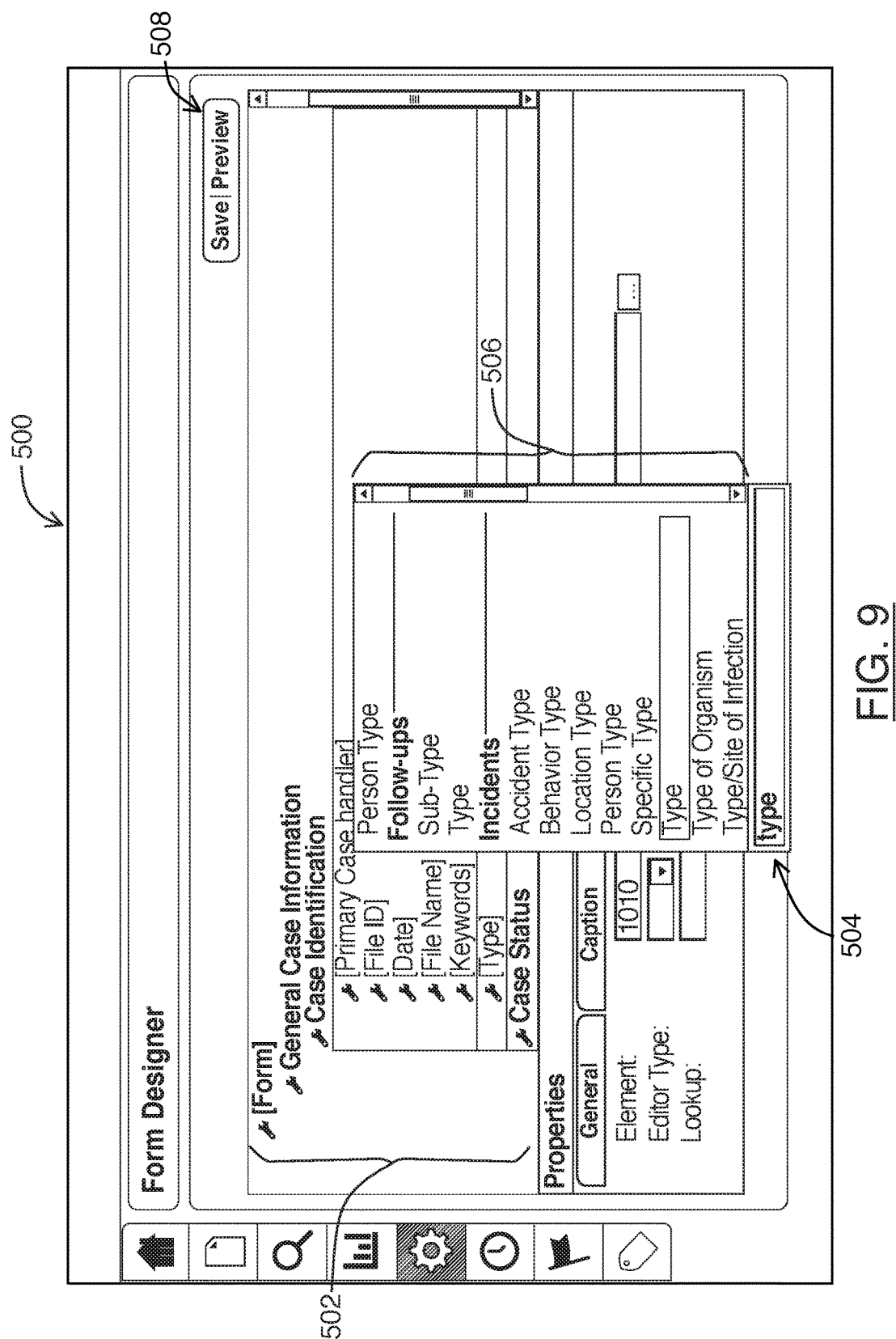
FIG. 9 is a screen shot diagram of a user interface component for receiving a selected field object to include in a form in accordance with an example embodiment.

FIG. 9 is a screen shot diagram of a user interface component 42 for receiving a selected field object to include in a form in accordance with an example embodiment. Interface module 24 is operable to provide a form designer 500. The form designer 500 may allow an administrator to select and choose form fields 502 to include in the form. Form fields 502 are instances of field objects stored in the dictionary within metabase 26. The selection of form fields 502 may be command driven, menu driven, or graphical interface driven.

Form designer 500 is operable to design a custom form. A form is an ordered set of form fields 502 stored within metabase 26. Upon receiving a request for a form, form engine 20 is operable to retrieve a form from metabase 26. Form designer 500 may provide tools for creating and modifying form. In some embodiments, form designer 502 is operable to organize the form using sections and clusters. Form designer 500 may organize the form, sections, clusters, and form fields in a tree. Each node in the tree is a field object.

In some embodiments, the form designer 502 is operable to provide a preview button 508 to generate a graphical representation of a finished form. In other embodiments, the form designer is operable to provide an interface that depicts a finished form as the administrator creates it (i.e., a so-called WYSIWYG editor).

Interface module 24 is operable to provide a search interface component 504 to aid an administrator in selecting form fields to include in a form. The search interface component 504 may be configured to receive input data, such as a name, one or more characters of a name, or a data type, for example, associated with a desired field object. A form field relating to case identification is desired in FIG. 9.

The search interface component 504 operates by initially providing an initial set of selectable field objects. The selectable field objects may be presented in a drop down list or within a pop out window, for example. This list may include every field object available to the administrator within the dictionary. In other embodiments, the list may be a subset of available field objects according to the cluster or section where the form field is being placed.

In some embodiments, the search interface component 504 is operable to receive input data associated with a desired field object in the set of selectable field objects. The received input data may be used to narrow the selection of possible field objects. For example, the interface module 24 may provide a search box for receiving input data at the search interface component 504. Alternatively, the interface module 24 may provide a series of checkboxes, radio buttons, or the like, to narrow the list of selectable field objects.

Upon entering input data, the search interface component 504 is operable to determine an updated set of selectable field objects 506. The updated set of selectable field objects 506 is a subset of the initial set of selectable field objects. Search interface component 504 may determine the subset based on one or more criteria. In FIG. 9, search interface component 504 receives a character string. This string may be used to narrow the set of selectable field objects based on the name of the field object. For example, a search for "Type" may return all field objects with the word "Type" in the name of the field object.

Alternatively, search interface component 504 is configured to use the input data to narrow the set of field objects based on the name or value of attributes of field objects. For example, the administrator may want to select a field object to include in the form that is mandatory or read-only. Search interface component 504 is operable to be flexible with the input data it receives and may cross reference the input data with known names and attributes. Entering "mandatory" into search interface component 504 may return field objects where either the name of the field object contains "mandatory" or where the "mandatory" presentation attribute in the field object is enabled. This provides additional flexibility for the administrator to locate a desired field object to include in a form.

In another example, an administrator may want to include a form field of a certain control type. Search interface component 504 is operable to search through the field values of one or more attributes to locate all field objects with the desired control type. A search for "list" may return an updated set of selectable field objects where either the name of the field object contains "list" or where the field value for control type (or other attribute of a field object) is "list".

Once search interface component 504 determines the subset of initial set of selectable field objects based on the received input data, the updated set of selectable field objects 506 provided to the form designer for selection by an administrator. Further, the search interface component 504 may operate dynamically such that the updated set of selectable field objects 506 is determined upon every character entry into a text box or every checkbox entered. Accordingly, the updated set of selectable field objects 506 may be narrowed upon every additional input data received.

Once an updated set of selectable field objects 506 is presented, an administrator may select a field object from the updated set. A form field corresponding to the selected field object will be included in the generated form.

A group of form fields may have a set of field value constraints. A set of field value constraints is a collection of all valid combinations of field values for each of the form fields. The combination information is stored in a matrix data structure stored with a form. The selection of a field value from a list of potential field values for any of the form fields results in the list of potential field values for each of the other form fields changing to a constrained set for each of the form fields based on the selected field value.

Field value constraints differ from traditional sequential drop down list constraints. Known systems include constraints on a group of form fields for selecting for selecting field values for related form fields, for example, an address location. For a traditional addressing embodiment, three form fields may be used to select a country, a province/state, and a city. When a country is selected from the list of potential field values (i.e., country names), the potential field values for province/state is limited to the province or state names that are within the selected country. Continuing on, once a province or state is selected, a list of potential field values relating to cities within the selected province or state is then available for selection.

Health care incident management system 12 is operable to implement an alternative to the above-mentioned traditional addressing embodiment. In at least one embodiment, health care incident management system 12 implements field value constraints for any form field without respect to any fixed sequence. Referring to the exemplary addressing embodiment, a user could select "Toronto" in a form field corresponding to the field object related to city. The field value constraints are operable to provide a constrained set of selectable field values corresponding to potential field values for province/state and country. The constrained set of selectable field values for country would be any country within the potential field values for country that have a city called "Toronto" in the country. Similarly, the constrained set of possible field values for province/state would be any province or state within the potential field values for province/state that have a city called "Toronto" within the province or state.

The flexibility of field value constraints is that a form field may receive a field value in any order. This may provide user convenience in a health care incident management system 12 where selections of a specific form field may significantly constrain the potential field values in the set of selectable field values for the other form fields.

Health care incident management system 12, of the present application, implements the above-mentioned field value constraints using a matrix data structure to store the possible combinations of potential field values.

Figures 10A, 10B, 10C:
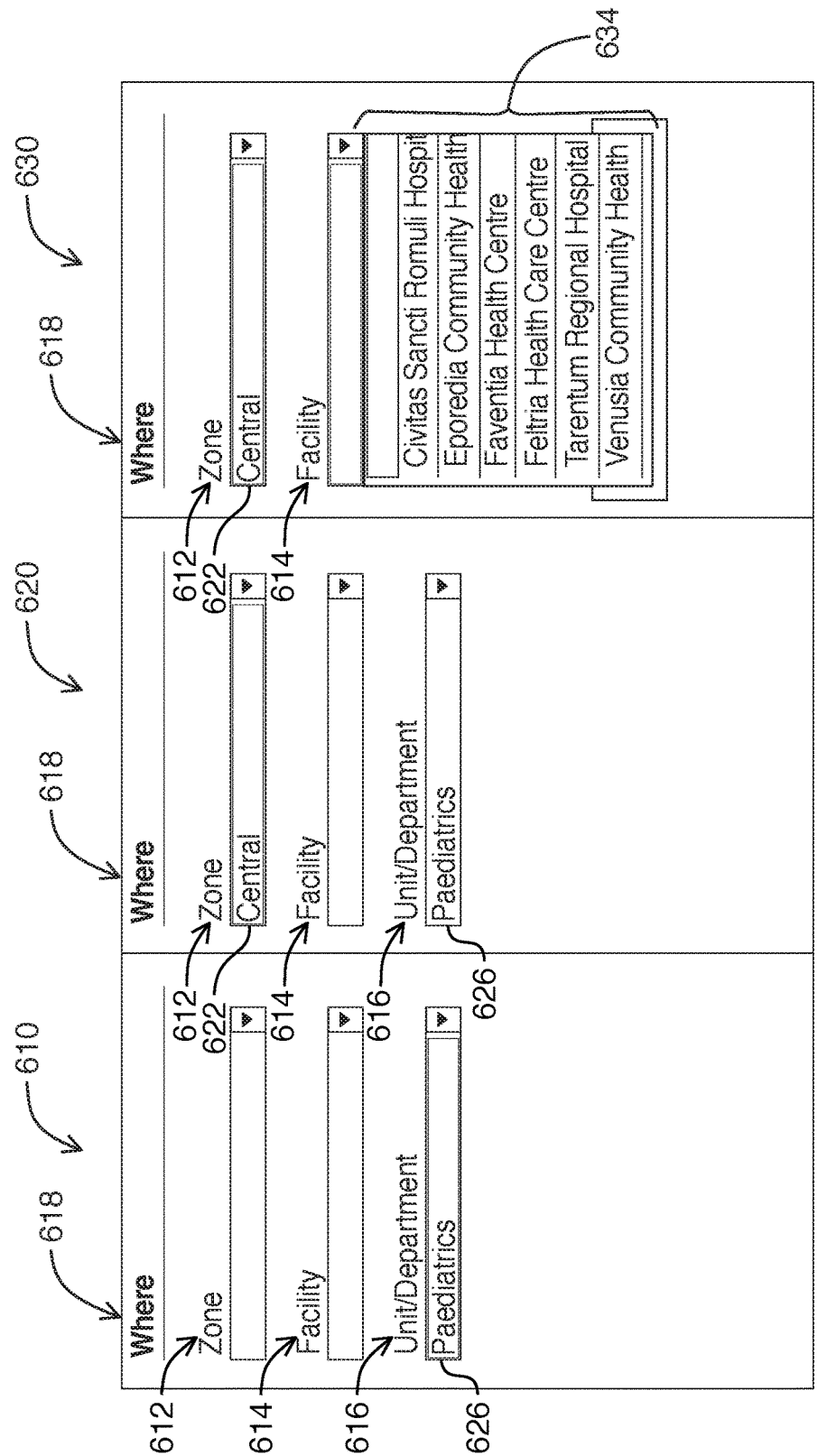
FIG. 10A is a screen shot diagram of a user interface component for receiving data in relation to a health care incident in accordance with an example embodiment.
FIG. 10B is a screen shot diagram of a user interface component for receiving data in relation to a health care incident in accordance with an example embodiment.
FIG. 10C is a screen shot diagram of a user interface component for receiving data in relation to a health care incident in accordance with an example embodiment.

Interface module 24 may provide additional user interface components to include in the form designer 500. FIG. 10A, FIG. 10B, FIG. 10C are screen shot diagrams 610, 620, 630 of a user interface component 42 for receiving data in relation to a health care incident in accordance with an example embodiment. In FIG. 10A, three form fields related to an incident location are arranged in a cluster 618 labeled "Where". Each form field is an instance of a field object 612, 614, 616. The three field objects in the cluster 618 are related to a zone 612, a facility 614 and a unit/department 616. Each field object 612, 614, 616 is defined by a drop down list of potential field values. User interface component 42 is operable to receive field values for the three related form fields upon selection by a user.

Figure 11:
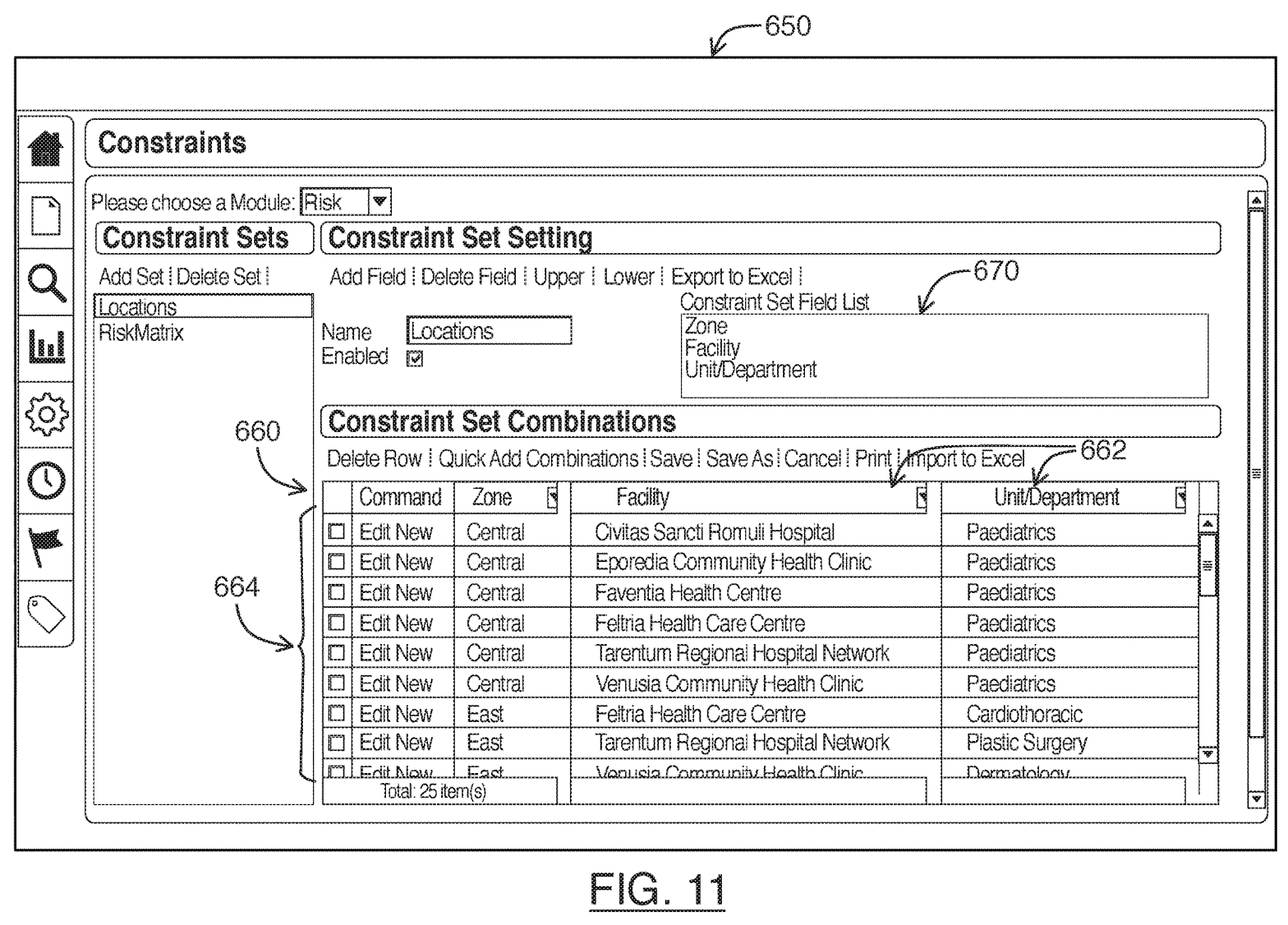

FIG. 11 is a screen shot diagram of a user interface component 42 for defining the matrix data structure 660 in accordance with an example embodiment. The columns 662 of the matrix may be the set of form fields 670 to be included in the constrained set of potential field values. The rows 664 of the matrix data structure 660 may be all possible combinations of field values for the different form fields. A matrix data structure 660 is faster than an implementation using conditional statements. For each selected field value in a form field 662, the user interface component 42 can reference the matrix data structure 660 to provide a constrained set of selectable field values for each of the other form fields 662. A single row 664 corresponds to a valid combination of form fields 662 in the set of form fields 670.

Each form field 662 in the set of form fields 670 is operable to receive a set of selectable field values. Each selectable field value corresponds to a potential field value for the form field. As a form field 662 is an instance of a field object, the potential field values associated with the corresponding field object are stored within metabase 26. Metabase 26 is operable to store the potential field values within a list type attribute associated with the corresponding field object.

A matrix data structure 660 is operable to link a field value for a first form field with a constrained set of selectable field values for each of the other form fields in the set of form fields 670. For example, in the addressing example, a matrix data structure 660 is operable to link the potential field value "Toronto" related to the city form field with different countries and provinces/states. A row 664 in the matrix data structure 660 is created for each possible field value combination of country and province/state where the field value of the city form field is "Toronto". For a health care incident management system 12 operating in at least North America, a constrained set of potential field values for province/state form field may include Ontario, Illinois, Indiana, Iowa, Kansas, Missouri and Ohio as selectable field values. Similarly, a constrained set of potential field values for the country form field may include Canada and the United States as selectable field values. A matrix data structure 660 is operable to create the two constrained sets of selectable field values when the possible combinations are entered as rows of the matrix 664.

The constrained set of selectable field values for each of the other form fields (i.e., province and country) is a subset of the set of potential field values for the respective form fields. Furthermore, the constrained sets of selectable field values for both province/state and country are related to the field value of "Toronto" for the city form field. When the selected field value from the set of selectable field values for the first field object is received, the constrained sets of selectable field values for each of the other form fields is provided.

The matrix data structure 620 is further operable for linking a field value for a second form field to a constrained set of selectable field values for each of the other form fields in the set of form fields and for linking a field value for a third form field to a constrained set of selectable field values for each of the other form fields in the set of form fields. The matrix data structure 620 is expandable to any number of form fields in the set of form fields. By defining a matrix where the rows of the matrix define every possible combination in the set of form fields, a constrained set of selectable field values for each of the other form fields can be easily defined.

FIG. 10A, FIG. 10B, and FIG. 10C depict the progression of selecting a field value for each of the different field objects 610, 612, 614. A field value corresponding to a field object 610, 612, 614 may be selected in any order. Interface module 24 is operable to receive a selected field value from the set of selectable field values for each of the field objects 610, 612, 614. When a field value is selected for any of the three form fields corresponding to the three field objects 610, 612, 614 the set of selectable field values for the other two form fields is constrained. Each possible combination of field values for the three form fields is stored as a row 664 in the matrix data structure 660.

In the first screen shot 610 depicted in FIG. 10A, the field value "Paediatrics" 626 is selected for the form field corresponding to a unit/department 616. This selection of a first field value 626 corresponding to a unit/department 616 constrains the set of selectable field values relating to a zone 612 and a facility 614. The constrained set of selectable field values for a zone 612 and a facility 614 are any field values in the set of potential field values of zones 612 and facilities 614 that have a paediatrics department.

In the second screen shot 620 depicted in FIG. 10B, paediatrics 626 is selected for a unit/department 616 and central 622 is selected for a zone 612. In some embodiments, a field value for a corresponding field object may be automatically selected if the constrained set of selectable field values is limited to a single option. In the second screen shot 620 of FIG. 10B, "Central" 622 may be selected automatically if no other zones 612 have a pediatrics unit 626.

In the third screen shot 630 depicted in FIG. 10C, a constrained set of selectable field values 634 is depicted for a form field corresponding to a facility 614. The constrained set of selectable field values 634 is a subset of the potential field values for facility 614. The constrained set of selectable field values 634 is comprised of the set of potential field values for a facility 614 that is in the zone 612 corresponding to central 622 and has a unit/department 616 for pediatrics 626.

Referring to FIG. 11, health care incident management system 12 is operable to provide an interface module 650 for defining a matrix data structure 660 for a form. The interface module 650 is operable to allow a user to create a set of field value constraints. Each row 664 in the matrix data structure 660 corresponds to a valid combination of field objects in the set of form fields 670. The columns 662 of the matrix data structure 660 correspond to the set of form fields 670.

Interface module 650 is operable to provide options for adding, deleting, editing, and saving changes to the matrix data structure 660. In addition, a column 662 may be sorted according to its potential field values. When defining the combinations of potential field values, an administrator may be able to easily identify the constrained set of selectable field values for the other field objects 610, 612, 614 in the set of form fields 670.

A user of health care incident management system 12 may access a form utilizing form engine 20 via workstation 16. Once the user has entered field values for each of the form fields, the form may be sent to metabase 26 for storage in persistent store 30. Interface module 24 is operable to receive field value data from the form fields in a form. The form fields are instances of corresponding field objects. The form field may also be instances of user-defined field objects. The interface module 24 is operable to determine the data location within the persistence store 30 linked to the user-defined field object. The interface module may reference metabase 26 to determine from metabase tables 28 the data location of a particular field object in persistent store 30. Health care incident management system 12 is operable to store the received field value data as a field value at the data location linked to the user-defined field object. This may involve a record being created in the persistent store 30 for the form. The field value data for the field object may be stored in the appropriate column or data location for the record created for the form.

Health care incident management system 12 is operable to provide reports to a user via report engine 22. Report engine 22 is operable to generate reports using data in metabase 26, including the stored field values in the persistent store 30. A report may include text, tables, figures, pictures, attachments, abstracts, summaries, appendices, footnotes, hyperlinks, charts, graphs and the like. For example, the report may be a medical incident report outlining all health care incidents involving a specific patient. As another example, a report may provide a summary of field value data received in relation to a specific health care incident.

Report engine 22 may generate a report using the field objects stored in the metabase 26. A report may use the field values stored in persistent store 30 corresponding to the user-defined field object. In some embodiments, a report may be a summary of the field values entered into a form. In other embodiments, reports may include additional processing and use field values from a number of completed forms. For example, a report for health care incident management system 12 may include a summary of a specific hospital incident. A report may also include a listing of all hospital incidents for the last year that occurred in a particular hospital section. In some embodiments, report engine 22 is operable to support a wide range of document formats incorporating one or more field objects stored in the metabase 26. For example, a report may be a text document, a word document, a pdf, an email, or any of a number of open document formats or proprietary document formats.

Report engine 22 is operable to receive a request to generate a report from a user using workstation 16 over network 14. The request may comprise a user identifier. The report may also include one or more search terms. In some embodiments, interface module 24 or user interface component 42 on workstation 16 may receive the request from a user to generate a report. Interface module 24 is operable to communicate a request to report engine 22 using a graphical user interface. Complex search queries may be generated and a report may be organized using interface module 24.

Figure 12:
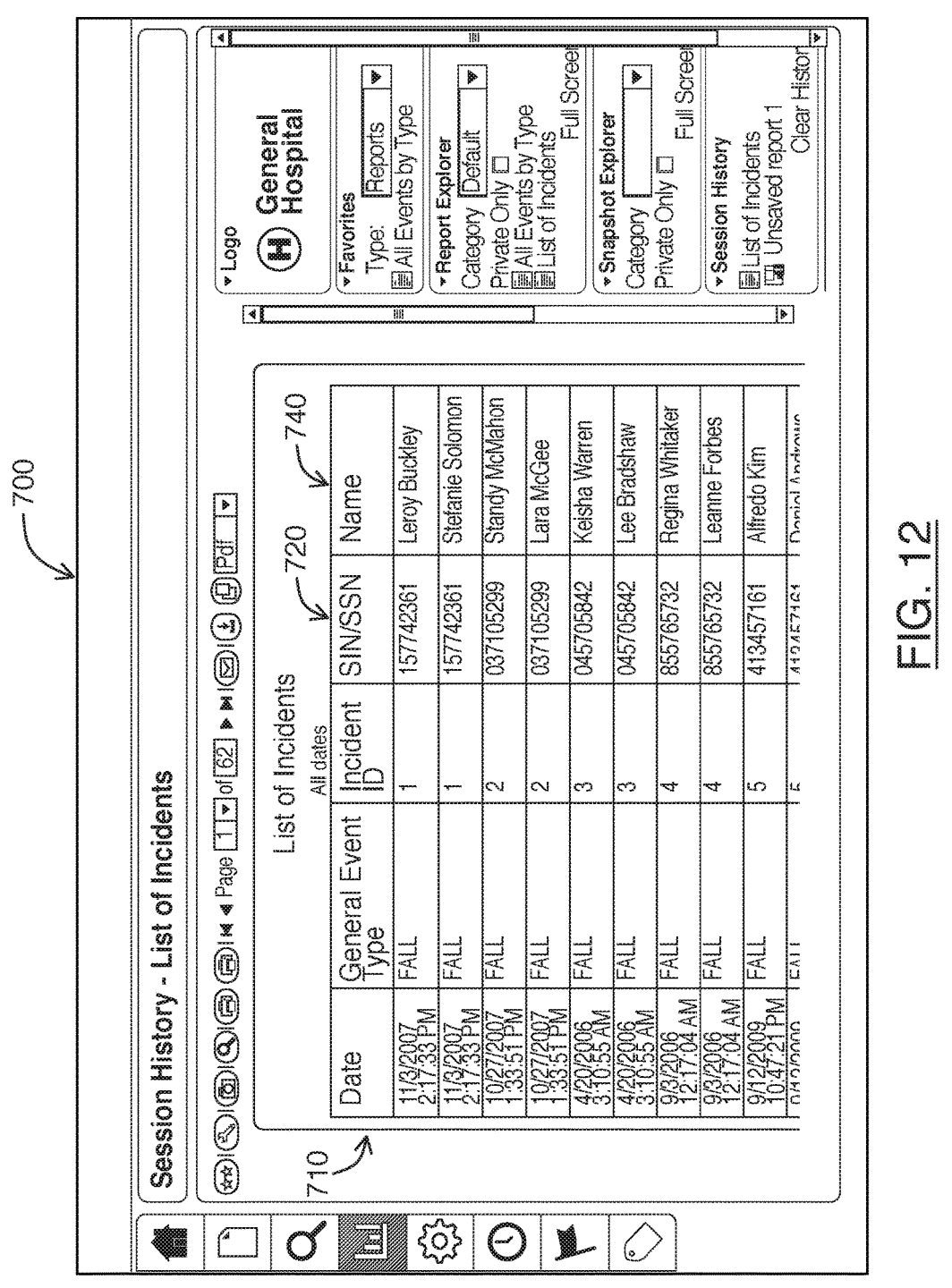

FIG. 12 is a screen shot diagram 700 of a report 710 in accordance with an example embodiment. Interface module 24 is operable to provide a report 710 to a workstation 16 via network 14. A report 710 comprises a collection of data values corresponding to field objects. In the exemplary report 710, a collection of incidents is presented with field values corresponding to Date, General Event Type, Incident ID, SIN/SSN 720 and Name 740. The report 710 is presented in the form of a table. Other formats are also possible for displaying field values. For example, information pertaining to field objects may be displayed as graphs, charts, plots, tables, and the like. Interface module 24 may be configured to provide tools for saving, printing and exporting the report 710.

Figure 14:
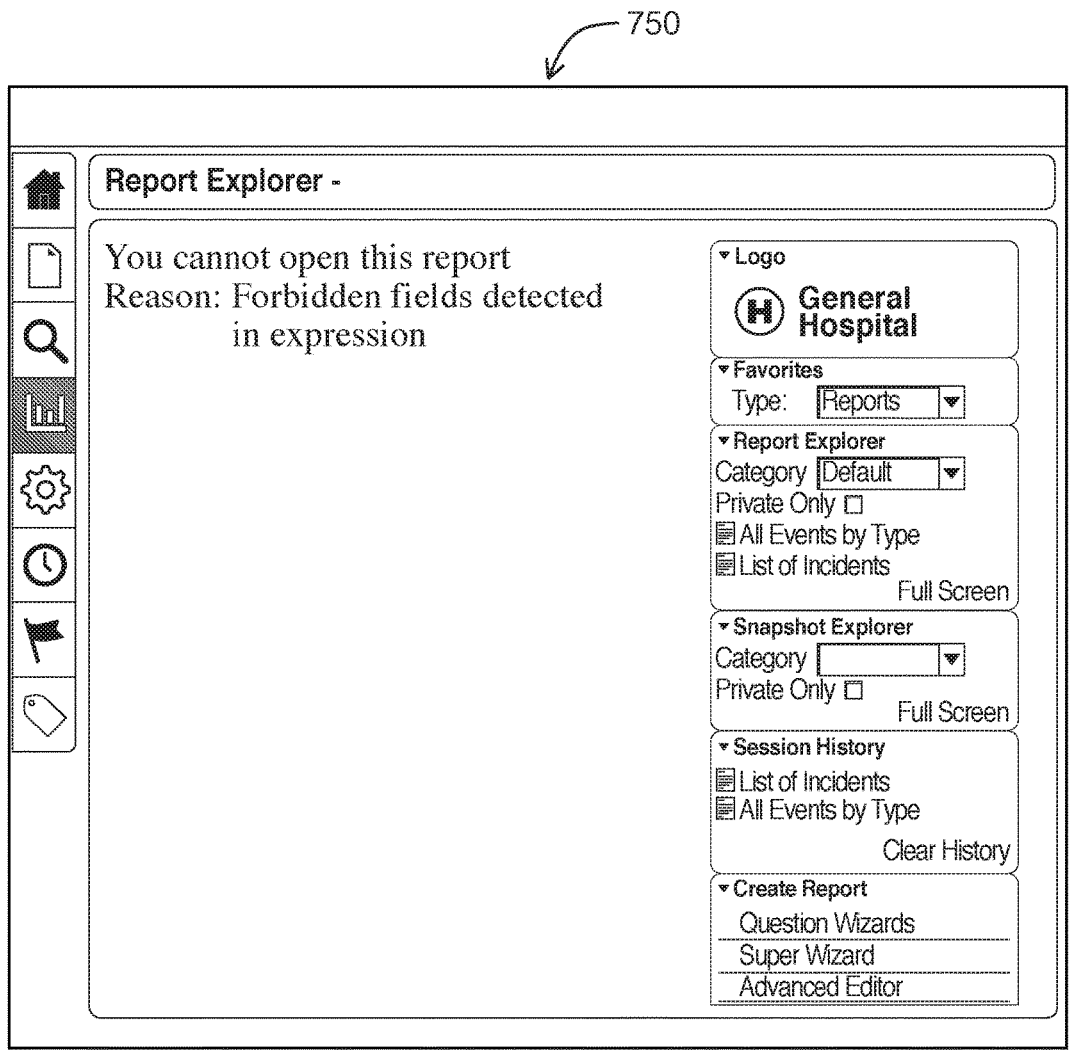
FIG. 14 is a screen shot diagram of a request for a report being rejected in accordance with an example embodiment.

In some embodiments, report engine 22 is operable to determine that the request comprising the at least one search term is a permitted search term using the user identifier. Health care incident management system 12 may refer to a user role and data scope to make this determination. Report engine 22 may reference access controls stored in metabase 26 to make such a determination. If a request for a report is not permitted, form engine 22 may return an error condition to interface module 24, which may inform the user that the request to generate a report is denied. Referring now to FIG. 14, report engine 22 has determined that the user identifier has tried to request a report using a forbidden field in the search query.

Metabase 26 is operable to store user roles and data scopes associated with user identifiers. A user role may include the user identifier's position within health care incident management system 12, i.e., a manager, a doctor, or a nurse. Certain user roles may be assigned different access rights pertaining to different reports.

Report engine 22 is operable to identify a plurality of field objects for generating the report. The report may correspond to a search term or a more complex search query. Report engine 22 is operable to determine that a field object is forbidden to the user identifier. A user identifier may have different data scopes that grant different privileges on a field value level. Health care incident management system 12 is operable to determine that the request to generate the report is a permitted search request according to the data scope associated with the user identifier.

In some embodiments, report engine 22 is operable to generate the report by removing data corresponding to the one or more field objects forbidden to the user identifier. Report engine 20 is operable to indicate that a forbidden field has been removed. The report may have replacement text, such as "Forbidden" in lieu of the forbidden field. In some instances, report engine 20 is configured to generate the report without indicating that the forbidden field has been removed. Form engine 20 may format the report to remove spaces and other indications that forbidden fields have been removed.

Figure 13:
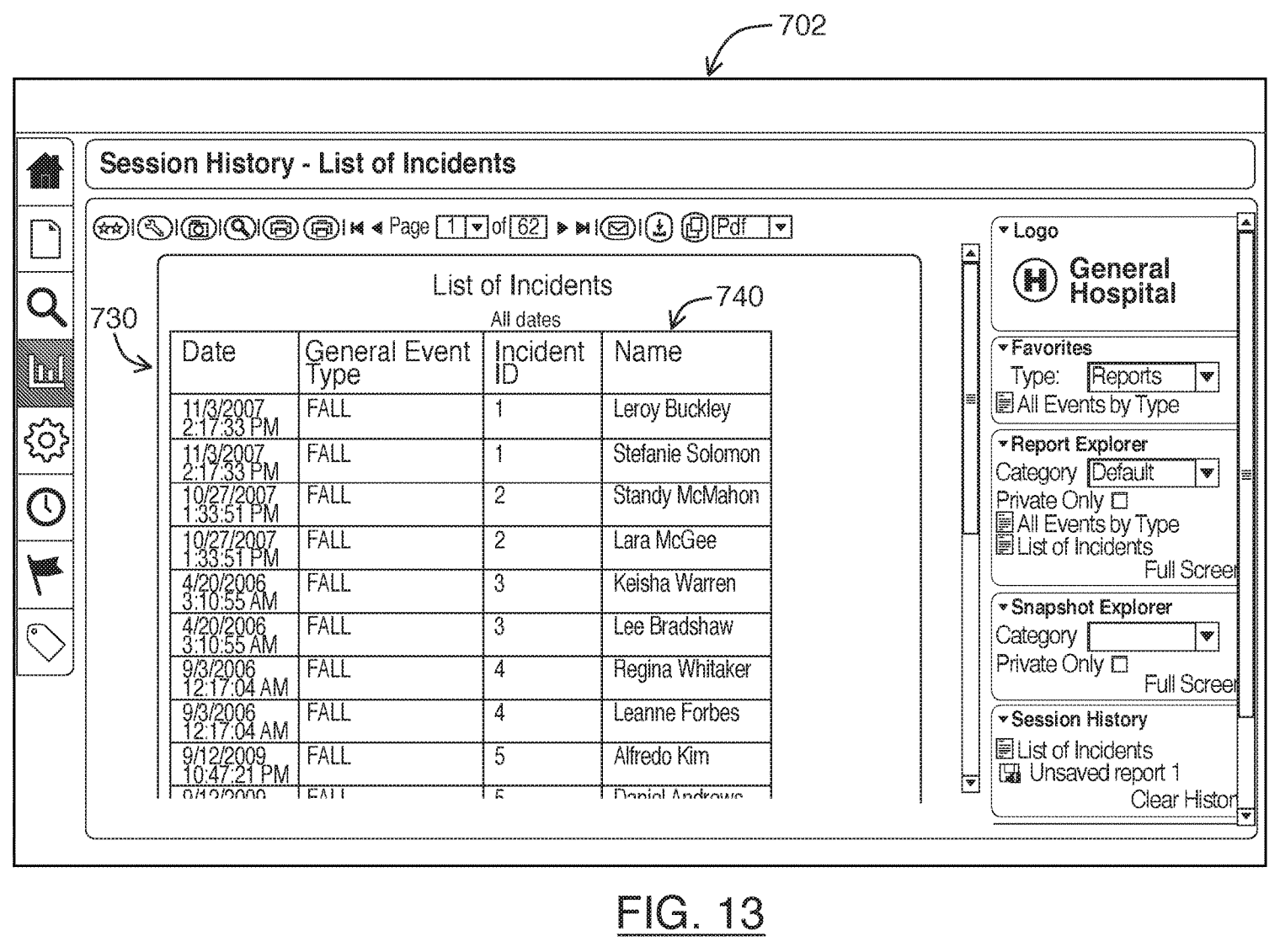

FIG. 13 is a screen shot diagram 702 of a report 730 in accordance with an example embodiment. In the exemplary report 730, a collection of incidents is presented with field values corresponding to Date, General Event Type, Incident ID, and Name 740. Briefly referencing FIG. 12, a column corresponding to SIN/SSN 720 has been removed from the report 730 depicted in FIG. 13. The column corresponding to name has been shifted to take its position.

Using the metabase 26, custom reports may be generated. Metabase 26 is operable to provide data abstraction and as benefit custom reports can be made that use different names for the same underlying field objects. This is useful as different reports can be generated using the same underlying data without having to manually relabel incorporated field objects. For example, custom reports are beneficial to different sections in a health care facility if they use different naming conventions for the same underlying data, such as "Birth Date" or "Date of Birth".

Reports on health care incidents for submission to certain reporting bodies or agencies may be required to use specific labels for certain field objects. For example, a form used to submit a health incident report to a specific reporting body might require "Surname" over a more common "Last Name". For example, exemplary reporting bodies may include: MedMarx, an Internet-accessible database that hospitals and health care systems use to track and trend adverse drug reactions and medication errors, operated by The United States Pharmacopeial Convention, and Canadian Medication Incident Reporting and Prevention System (CMIRPS), a medication incident tracking system operated by the Institute for Safe Medication Practices, Canada.

User-defined field objects are beneficial for custom reports where the report requests data that is not within the dictionary. Creating a user-defined field object allows the corresponding field value to be collected and stored by health care incident management system 12 for report generation. The flexibility of metabase 26 allows these custom reports to be easily created, stored and generated.

Once a report is generated, the user may decide to print the report or export the report to another application. Further, a generated report may be stored in health care incident management system 12 or in storage 18 for further processing.

The present invention has been described here by way of example only. Various modification and variations may be made to these exemplary embodiments without departing from the spirit and scope of the invention, which is limited only by the appended claims.

We claim:

1. A computer-implemented method for dynamically generating an electronic form for receiving electronic data relating to a health care incident at a user interface component, the electronic form adapted to provide a flexible meta-schema allowing a new or modified taxonomy to be adopted or accommodated without modifications to applications that process the electronic form, the method comprising:

providing a healthcare incident management system including a storage device and a processor, the storage device having a metabase associated therewith to maintain the meta-schema and the processor configured to provide a form engine and a system interface;

providing a dictionary of field objects in a metabase, wherein an instance of a field object is a form field and wherein the form field is configured to receive a field value, the metabase structuring the dictionary of field objects into corresponding meta-tables and establishing meta-relations defining parent-child relationships between nodes representing the one or more field objects of the metabase, the meta-relations being maintained as corresponding foreign keys used to reference the corresponding field objects and the corresponding meta-tables, the metabase configured to have a dynamic number of columns that is dynamic according to a number of field objects in the dictionary;

adding one or more additional user-defined field objects in the metabase representing the new or modified taxonomy;

automatically maintaining, by the metabase, electronic representations of relationships between the field objects and the corresponding form fields, the automatic maintaining including:
  establishing, by the metabase, one or more new columns corresponding to the one or more additional user-defined field objects; and
  establishing new meta-relations defining the one or more additional user-defined field objects as new child nodes to corresponding parent nodes of the one or more additional user-defined field objects;
  generating the form, wherein the form comprises an ordered collection of form fields, wherein at least one form field is configured to receive data relating to a health care incident, and wherein at least one form field is an instance of the user-defined field object, the ordered collection based at least on the relationships stored in the metabase including at least the meta-tables, the meta-relations, and the new meta-relations, the new meta-relations adopting or accommodating the new or modified taxonomy; and
  controlling the display to automatically return and display the ordered collection of form fields.

2. The method of claim 1, further comprising, prior to the step of generating the electronic form, the steps of:
  receiving a request to create a user-defined field object;
  determining, using the processor, that the user-defined field object is not in the dictionary of field objects in the metabase;
  generating, using the processor, the user-defined field object by defining attributes for the user-defined field object, wherein at least one attribute is a presentation attribute for a form field within the electronic form;
  adding the user-defined field object to the dictionary of field objects in the metabase; and
  linking the user-defined field object to a data location in the storage device.

3. The method of claim 2, further comprising:
  receiving field value data at the form field that is an instance of the user-defined field object;
  determining the data location within the storage device linked to the user-defined field object; and
  storing the received field value data as a field value at the data location linked to the user-defined field object.

4. The method of claim 2, wherein defining attributes corresponding to the user-defined field object comprises:
  providing a set of selectable attributes;
  receiving at least one selected attribute; and
  defining the at least one selected attribute as an attribute for the user-defined field object.

5. The method of claim 4, further comprising:
  providing a set of selectable attribute values based on the selected attribute;
  receiving at least one selected attribute value; and
  linking the at least one selected attribute value to the selected attribute linked to the user-defined field object.

6. The method of claim 1 wherein the attributes are selected from the group consisting of: primary key identifier; version; last user to modify; time of last modification; table identifier; field name; field caption; field description; kind; database field name; field type; sequence; transient; allow null; unique; boolean default value; datetime default value; datetime mode; decimal default value; decimal is money; decimal precision; decimal scale; expression; kind of expression; identity auto increment; identity auto increment seed; identity auto increment step; identity default value; integer default value; number default value; text default value; maximum length of text; timespan default value; terminology provider; terminology namespace; terminology concept; mandatory; read-only; visible; extra parameters; list name; cachable; default value; security token; availability; field caption; control type; private; user created; identity use; inter default value and verification mask.

7. The method of claim 3, further comprising:
  generating, via the processor, an electronic report using the field value corresponding to the user-defined field object.

8. The method of claim 7 further comprising:
  receiving a request to generate the electronic report, wherein the request to generate the electronic report includes a user identifier and at least one search term;
  determining that the request to generate the electronic report is a permitted search request using the user identifier;
  identifying a plurality of field objects for generating the report;
  determining that one or more of the plurality of field objects is forbidden to the user identifier; and
  generating the report using the plurality of field objects and excluding data corresponding to the one or more field objects forbidden to the user identifier.

9. The method of claim 1 wherein generating the electronic form comprises:
  providing an initial set of selectable field objects;
  providing a search interface component configured to receive input data associated with a field object in the set of selectable field objects;
  receiving input data at the search interface component;
  determining an updated set of selectable field objects using the received input data;
  providing the updated set of selectable field objects, wherein the updated set of selectable field objects is a subset of the initial set of selectable field objects;
  receiving a selected field object from the updated set; and
  generating the electronic form using the form field that is an instance of the selected field object.

10. The method of claim 1, wherein the request includes a user identifier, and the generating a form further comprises:
  associating the user identifier with a user role, wherein the user role defines a data scope, wherein the data scope defines a set of permitted form fields;
  determining that the request to generate the electronic form is a permitted search request according to the data scope associated with the user identifier; and
  limiting the collection of form fields in the electronic form according to the data scope associated with the user identifier.

11. The method of claim 2 further comprises:
  arranging the dictionary of field objects in the metabase as a tree of nodes, wherein each node corresponds to a field object.

12. A computer system for dynamically generating an electronic form for receiving electronic data relating to a health care incident, the electronic form adapted to provide a flexible meta-schema allowing a new or modified taxonomy to be adopted or accommodated without modifications to applications that process the electronic form, the system comprising:
  a user interface component on a connected device configured to receive a request to create the form;
  a storage device having a metabase associated therewith to maintain the meta-schema; and
  at least one processor configured to execute instructions to provide a form engine and a system interface, the form engine configured to:

establish a communication link between the system interface and the user interface component over a network, receive, at the system interface from the user interface component via the network, the request to generate the electronic form using the form engine, store in the storage device, a dictionary of field objects in the metabase, wherein an instance of a field object is a form field, and wherein the form field is configured to receive a field value, the metabase structuring the dictionary of field objects into corresponding meta-tables and establishing meta-relations defining parent-child relationships between nodes representing the one or more field objects of the metabase, the meta-relations being maintained as corresponding foreign keys used to reference the corresponding field objects and the corresponding meta-tables, the metabase configured to have a dynamic number of columns that is dynamic according to a number of field objects in the dictionary, process the request from the user interface component to create the electronic form, add one or more additional user-defined field objects in the metabase, automatically maintain, by the metabase, electronic representations of relationships between the field objects and the form fields, the one or more additional user-defined field objects representing the new or modified taxonomy, the form engine configured to automatic maintain the electronic representations by:
establishing, by the metabase, one or more new columns corresponding to the one or more additional user-defined field objects; and
establishing new meta-relations defining the one or more additional user-defined field objects as new child nodes to corresponding parent nodes of the one or more additional user-defined field objects, generate the electronic form for the user interface component, wherein the form includes an ordered collection of form fields instantiated using the field objects, the ordered collection based at least on the relationships stored in the metabase including at least the meta-tables, the meta-relations, and the new meta-relations, control the display to automatically return and display, from the system interface to the user interface component, the electronic form along with a set of selectable field values for each form field in the electronic form, wherein each selectable field value corresponds to a potential field value associated with the corresponding field object used to instantiate the form field; and control the electronic form using the relationships stored in the metabase to adopt or accommodate the new or modified taxonomy.

13. The system of claim 12 wherein:
the user interface component is further configured to receive a request to create a user-defined field object;
the at least one processor is further configured to:
determine that the requested user-defined field object is not in the dictionary of field objects in the metabase;
generate the user-defined field object by defining attributes for the user-defined field object, wherein at least one attribute is a presentation attribute for a form field within the electronic form;
add the user-defined field object to the dictionary of field objects in the metabase; and
link the user-defined field object to a data location in the storage device.

14. The system of claim 12 wherein
the system interface is configured to receive field value data at the form field that is an instance of the user-defined field object; and
the metabase is further configured to store the received field value data as a field value at the data location linked to the user-defined field object.

15. The system of claim 13 wherein
the system interface is configured to provide a set of selectable attributes and receive at least one selected attribute; and
the metabase is further configured to define the at least one selected attribute as at least one attribute for the user-defined field object.

16. The system of claim 13 wherein
the system interface is further configured to provide a set of selectable attribute values based on at least one selected attribute and to receive at least one selected attribute value; and
the metabase is further configured to link the at least one selected attribute value to at least one attribute linked to the user-defined field object.

17. The system of claim 14 further comprising:
a report engine configured to generate, via the processor, an electronic report using the field value corresponding to the user-defined field object.

18. The system of claim 17 wherein the processor is further configured to,
receive a request to generate the electronic report, wherein the request to generate the electronic report includes a user identifier and at least one search term; and wherein the report engine is further configured to:
determine that the request to generate the electronic report is a permitted search request using the user identifier;
identify a plurality of field objects for generating the report;
determine that one or more of the plurality of field objects is forbidden to the user identifier; and
generate the report using the plurality of field objects and excluding data corresponding to the one or more field objects forbidden to the user identifier.

19. The system of claim 13 wherein
the interface module is further configured to:
provide an initial set of selectable field objects,
provide a search interface component configured to receive input data associated with a field object in the initial set of selectable field objects,
receive input data at the search interface component,
determine an updated set of selectable field objects using the received input data,
provide the updated set of selectable field objects, wherein the updated set of selectable field objects is a subset of the initial set of selectable field objects, and
receive a selected field object from the updated set; and
wherein the form engine is further configured to generate the electronic form using the form field that is an instance of the selected field object.

20. The system of claim 13 wherein
the interface module is further configured to receive a request to generate the form, the request to generate the form including a user identifier; and the form engine is further configured to:

associate the user identifier with a user role, wherein the user role defines a data scope, wherein the data scope defines a set of permitted form fields, determine that the request to generate the electronic form is a permitted search request according to the data scope associated with the user identifier, and limit the collection of form fields in the electronic form according to the data scope associated with the user identifier.

21. A data storage and retrieval system for a computer having a memory, a central processing unit, and a display, adapted to generate an electronic form for receiving electronic data relating to a health care incident, the electronic form adapted to provide a flexible meta-schema allowing a new or modified taxonomy to be adopted or accommodated without modifications to applications that process the electronic form, the electronic form including an ordered collection of form fields, each form field configured to receive a field value that is operatively linked to a corresponding field object, the data storage and retrieval system comprising:

a data storage device adapted to configure a metabase maintaining the meta-schema;

the central processing unit is configured to:

receive a request to generate the electronic form, store in the data storage device, a dictionary of field objects in the metabase, wherein an instance of a field object is a form field, and wherein the form field is configured to receive a field value that is operatively linked to a corresponding field object, the metabase structuring the dictionary of field objects into corresponding meta-tables and establishing meta-relations defining parent-child relationships between nodes representing the one or more field objects of the metabase, the meta-relations being maintained as corresponding foreign keys used to reference the corresponding field objects and the corresponding meta-tables, the metabase configured to have a dynamic number of columns that is dynamic according to a number of field objects in the dictionary, process the request to create the electronic form, add one or more additional user-defined field objects in the metabase, automatically maintain, by the metabase, electronic representations of relationships between the field objects and the form fields, the one or more additional user-defined field objects representing the new or modified taxonomy, the form engine configured to, when the one or more additional user-defined field objects are added to the metabase:

establish, in the metabase, one or more new columns corresponding to the one or more additional user-defined field objects; and establish new meta-relations defining the one or more additional user-defined field objects as new child nodes to corresponding parent nodes of the one or more additional user-defined field objects, generate the electronic form for presentment on the display, wherein the form includes an ordered collection of form fields instantiated using the field objects, the ordered collection based at least on the relationships stored in the metabase including at least the meta-tables, the meta-relations, and the new meta-relations, control the display to automatically return and display the electronic form along with a set of selectable field values for each form field in the electronic form, wherein each selectable field value corresponds to a potential field value associated with the corresponding field object used to instantiate the form field, wherein the electronic form is controlled based at least on the relationships stored in the metabase to adopt or accommodate the new or modified taxonomy.

* * * * *